(12) United States Patent
Blum et al.

(10) Patent No.: US 9,867,989 B2
(45) Date of Patent: Jan. 16, 2018

(54) PROGRAMMING INTERFACE FOR SPINAL CORD NEUROMODULATION

(71) Applicant: BOSTON SCIENTIFIC NEUROMODULATION CORPORATION, Valencia, CA (US)

(72) Inventors: David Arthur Blum, Boston, MA (US); Gregory T. Schulte, Minneapolis, MN (US); Scott Kokones, Boston, MA (US); Keith Carlton, Boston, MA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 383 days.

(21) Appl. No.: 14/537,299

(22) Filed: Nov. 10, 2014

(65) Prior Publication Data

US 2015/0066111 A1 Mar. 5, 2015

Related U.S. Application Data

(62) Division of application No. 13/160,104, filed on Jun. 14, 2011, now Pat. No. 8,913,804.

(Continued)

(51) Int. Cl.
*A61N 1/39* (2006.01)
*A61N 1/36* (2006.01)
(Continued)

(52) U.S. Cl.
CPC ............ *A61N 1/36182* (2013.01); *A61B 6/12* (2013.01); *A61B 90/37* (2016.02);
(Continued)

(58) Field of Classification Search
CPC ........ A61N 1/36182; A61B 90/37; A61B 6/12
See application file for complete search history.

(56) References Cited

U.S. PATENT DOCUMENTS

| 3,999,555 A | 12/1976 | Person |
| 4,144,889 A | 3/1979 | Tyers et al. |

(Continued)

FOREIGN PATENT DOCUMENTS

| EP | 1048320 | 11/2000 |
| EP | 1166819 | 1/2002 |

(Continued)

OTHER PUBLICATIONS

Nowinski, W. L., et al., "Statistical analysis of 168 bilateral subthalamic nucleus implantations by means of the probabilistic functional atlas.", Neurosurgery 57(4 Suppl) (Oct. 2005), 319-30.

(Continued)

*Primary Examiner* — Gregory M Desire
(74) *Attorney, Agent, or Firm* — Lowe Graham Jones PLLC; Bruce E. Black

(57) ABSTRACT

A tool for assisting in the planning or performing of electrical neuromodulation of a patient's spinal cord. The tool may have various functions and capabilities, including calculating a volume of activation, registering an electrode(s) shown in a radiologic image, constructing functional images of the patient's spinal anatomy, targeting of neuromodulation, finding a functional midline between multiple electrodes, determining the three-dimensional position of multiple electrodes, and/or accommodating for electrode migration. In certain embodiments, the tool can be embodied as computer software or a computer system.

19 Claims, 12 Drawing Sheets

Related U.S. Application Data

(60) Provisional application No. 61/354,576, filed on Jun. 14, 2010, provisional application No. 61/376,439, filed on Aug. 24, 2010.

(51) Int. Cl.
*A61B 6/12* (2006.01)
*A61N 1/372* (2006.01)
*G06F 19/00* (2011.01)
*A61B 6/00* (2006.01)
*A61B 90/00* (2016.01)

(52) U.S. Cl.
CPC ..... *A61N 1/36071* (2013.01); *A61N 1/36132* (2013.01); *A61N 1/37235* (2013.01); *G06F 19/3437* (2013.01); *A61B 6/506* (2013.01); *A61B 2090/368* (2016.02); *A61B 2090/376* (2016.02); *A61N 1/37247* (2013.01); *G06F 19/321* (2013.01); *G06F 19/324* (2013.01)

(56) References Cited

U.S. PATENT DOCUMENTS

| | | |
|---|---|---|
| 4,177,818 A | 12/1979 | De Pedro |
| 4,341,221 A | 7/1982 | Testerman |
| 4,378,797 A | 4/1983 | Osterholm |
| 4,445,500 A | 5/1984 | Osterholm |
| 4,735,208 A | 4/1988 | Wyler et al. |
| 4,765,341 A | 8/1988 | Mower et al. |
| 4,841,973 A | 6/1989 | Stecker |
| 5,067,495 A | 11/1991 | Brehm |
| 5,099,846 A | 3/1992 | Hardy |
| 5,222,494 A | 6/1993 | Baker, Jr. |
| 5,255,693 A | 10/1993 | Dutcher |
| 5,259,387 A | 11/1993 | dePinto |
| 5,304,206 A | 4/1994 | Baker, Jr. et al. |
| 5,344,438 A | 9/1994 | Testerman et al. |
| 5,361,763 A | 11/1994 | Kao et al. |
| 5,452,407 A | 9/1995 | Crook |
| 5,560,360 A | 10/1996 | Filler et al. |
| 5,565,949 A | 10/1996 | Kasha, Jr. |
| 5,593,427 A | 1/1997 | Gliner et al. |
| 5,601,612 A | 2/1997 | Gliner et al. |
| 5,607,454 A | 3/1997 | Cameron et al. |
| 5,620,470 A | 4/1997 | Gliner et al. |
| 5,651,767 A | 7/1997 | Schulmann |
| 5,711,316 A | 1/1998 | Elsberry et al. |
| 5,713,922 A | 2/1998 | King |
| 5,716,377 A | 2/1998 | Rise et al. |
| 5,724,985 A | 3/1998 | Snell et al. |
| 5,749,904 A | 5/1998 | Gliner et al. |
| 5,749,905 A | 5/1998 | Gliner et al. |
| 5,776,170 A | 7/1998 | MacDonald et al. |
| 5,782,762 A | 7/1998 | Vining |
| 5,843,148 A | 12/1998 | Gijsbers et al. |
| 5,859,922 A | 1/1999 | Hoffmann |
| 5,868,740 A | 2/1999 | LeVeen et al. |
| 5,897,583 A | 4/1999 | Meyer et al. |
| 5,910,804 A | 6/1999 | Fortenbery et al. |
| 5,925,070 A | 7/1999 | King et al. |
| 5,938,688 A | 8/1999 | Schiff |
| 5,938,690 A | 8/1999 | Law et al. |
| 5,978,713 A | 11/1999 | Prutchi et al. |
| 6,016,449 A | 1/2000 | Fischell et al. |
| 6,029,090 A | 2/2000 | Herbst |
| 6,029,091 A | 2/2000 | de la Rama et al. |
| 6,050,992 A | 4/2000 | Nichols |
| 6,058,331 A | 5/2000 | King |
| 6,066,163 A | 5/2000 | John |
| 6,083,162 A | 7/2000 | Vining |
| 6,094,598 A | 7/2000 | Elsberry et al. |
| 6,096,756 A | 8/2000 | Crain et al. |
| 6,106,460 A | 8/2000 | Panescu et al. |
| 6,109,269 A | 8/2000 | Rise et al. |
| 6,128,538 A | 10/2000 | Fischell et al. |
| 6,129,685 A | 10/2000 | Howard, III |
| 6,146,390 A | 11/2000 | Heilbrun et al. |
| 6,161,044 A | 12/2000 | Silverstone |
| 6,167,311 A | 12/2000 | Rezai |
| 6,181,969 B1 | 1/2001 | Gord |
| 6,192,266 B1 | 2/2001 | Dupree et al. |
| 6,205,361 B1 | 3/2001 | Kuzma |
| 6,208,881 B1 | 3/2001 | Champeau |
| 6,240,308 B1 | 5/2001 | Hardy et al. |
| 6,246,912 B1 | 6/2001 | Sluijter et al. |
| 6,253,109 B1 | 6/2001 | Gielen |
| 6,289,239 B1 | 9/2001 | Panescu et al. |
| 6,301,492 B1 | 10/2001 | Zonenshayn |
| 6,310,619 B1 | 10/2001 | Rice |
| 6,319,241 B1 | 11/2001 | King et al. |
| 6,336,899 B1 | 1/2002 | Yamazaki |
| 6,343,226 B1 | 1/2002 | Sunde et al. |
| 6,351,675 B1 | 2/2002 | Tholen et al. |
| 6,353,762 B1 | 3/2002 | Baudino et al. |
| 6,366,813 B1 | 4/2002 | Dilorenzo |
| 6,368,331 B1 | 4/2002 | Front et al. |
| 6,389,311 B1 | 5/2002 | Whayne et al. |
| 6,393,325 B1 | 5/2002 | Mann et al. |
| 6,421,566 B1 | 7/2002 | Holsheimer |
| 6,435,878 B1 | 8/2002 | Reynolds et al. |
| 6,442,432 B2 | 8/2002 | Lee |
| 6,463,328 B1 | 10/2002 | John |
| 6,491,699 B1 | 12/2002 | Henderson et al. |
| 6,494,831 B1 | 12/2002 | Koritzinsky |
| 6,507,759 B1 | 1/2003 | Prutchi et al. |
| 6,510,347 B2 | 1/2003 | Borkan |
| 6,516,227 B1 | 2/2003 | Meadows et al. |
| 6,517,480 B1 | 2/2003 | Krass |
| 6,539,263 B1 | 3/2003 | Schiff et al. |
| 6,560,490 B2 | 5/2003 | Grill et al. |
| 6,579,280 B1 | 6/2003 | Kovach et al. |
| 6,600,956 B2 | 7/2003 | Maschino et al. |
| 6,606,523 B1 | 8/2003 | Jenkins |
| 6,609,029 B1 | 8/2003 | Mann et al. |
| 6,609,031 B1 | 8/2003 | Law et al. |
| 6,609,032 B1 | 8/2003 | Woods et al. |
| 6,622,048 B1 | 9/2003 | Mann et al. |
| 6,631,297 B1 | 10/2003 | Mo |
| 6,654,642 B2 | 11/2003 | North et al. |
| 6,662,053 B2 | 12/2003 | Borkan |
| 6,675,046 B2 | 1/2004 | Holsheimer |
| 6,684,106 B2 | 1/2004 | Herbst |
| 6,687,392 B1 | 2/2004 | Touzawa et al. |
| 6,690,972 B2 | 2/2004 | Conley et al. |
| 6,690,974 B2 | 2/2004 | Archer et al. |
| 6,692,315 B1 | 2/2004 | Soumillion et al. |
| 6,694,162 B2 | 2/2004 | Hartlep |
| 6,694,163 B1 | 2/2004 | Vining |
| 6,708,096 B1 | 3/2004 | Frei et al. |
| 6,741,892 B1 | 5/2004 | Meadows et al. |
| 6,748,098 B1 | 6/2004 | Rosenfeld |
| 6,748,276 B1 | 6/2004 | Daignault, Jr. et al. |
| 6,778,846 B1 | 8/2004 | Martinez et al. |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,845,267 B2 | 1/2005 | Harrison et al. |
| 6,850,802 B2 | 2/2005 | Holsheimer |
| 6,895,280 B2 | 5/2005 | Meadows et al. |
| 6,909,913 B2 | 6/2005 | Vining |
| 6,937,891 B2 | 8/2005 | Leinders et al. |
| 6,937,903 B2 | 8/2005 | Schuler et al. |
| 6,944,497 B2 | 9/2005 | Stypulkowski |
| 6,944,501 B1 | 9/2005 | Pless |
| 6,950,707 B2 | 9/2005 | Whitehurst |
| 6,969,388 B2 | 11/2005 | Goldman et al. |
| 7,003,349 B1 | 2/2006 | Andersson et al. |
| 7,003,352 B1 | 2/2006 | Whitehurst |
| 7,008,370 B2 | 3/2006 | Tanner et al. |
| 7,008,413 B2 | 3/2006 | Kovach et al. |
| 7,035,690 B2 | 4/2006 | Goetz |
| 7,043,293 B1 | 5/2006 | Baura |

(56) References Cited

U.S. PATENT DOCUMENTS

| | | |
|---|---|---|
| 7,047,082 B1 | 5/2006 | Schrom et al. |
| 7,047,084 B2 | 5/2006 | Erickson et al. |
| 7,050,857 B2 | 5/2006 | Samuelsson et al. |
| 7,054,692 B1 | 5/2006 | Whitehurst et al. |
| 7,058,446 B2 | 6/2006 | Schuler et al. |
| 7,082,333 B1 | 7/2006 | Bauhahn et al. |
| 7,107,102 B2 | 9/2006 | Daignault, Jr. et al. |
| 7,126,000 B2 | 10/2006 | Ogawa et al. |
| 7,127,297 B2 | 10/2006 | Law et al. |
| 7,136,518 B2 | 11/2006 | Griffin et al. |
| 7,136,695 B2 | 11/2006 | Pless et al. |
| 7,142,923 B2 | 11/2006 | North et al. |
| 7,146,219 B2 | 12/2006 | Sieracki et al. |
| 7,146,223 B1 | 12/2006 | King |
| 7,151,961 B1 | 12/2006 | Whitehurst et al. |
| 7,155,279 B2 | 12/2006 | Whitehurst et al. |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,191,014 B2 | 3/2007 | Kobayashi et al. |
| 7,209,787 B2 | 4/2007 | DiLorenzo |
| 7,211,050 B1 | 5/2007 | Caplygin |
| 7,216,000 B2 | 5/2007 | Sieracki et al. |
| 7,217,276 B2 | 5/2007 | Henderson et al. |
| 7,218,968 B2 | 5/2007 | Condie et al. |
| 7,228,179 B2 | 6/2007 | Campen et al. |
| 7,231,254 B2 | 6/2007 | DiLorenzo |
| 7,236,830 B2 | 6/2007 | Gliner |
| 7,239,910 B2 | 7/2007 | Tanner |
| 7,239,916 B2 | 7/2007 | Thompson et al. |
| 7,239,926 B2 | 7/2007 | Goetz |
| 7,242,984 B2 | 7/2007 | DiLorenzo |
| 7,244,150 B1 | 7/2007 | Brase et al. |
| 7,252,090 B2 | 8/2007 | Goetz |
| 7,254,445 B2 | 8/2007 | Law et al. |
| 7,254,446 B1 | 8/2007 | Erickson et al. |
| 7,257,447 B2 | 8/2007 | Cates et al. |
| 7,266,412 B2 | 9/2007 | Stypulkowski |
| 7,294,107 B2 | 11/2007 | Simon et al. |
| 7,295,876 B1 | 11/2007 | Erickson |
| 7,299,096 B2 | 11/2007 | Balzer et al. |
| 7,308,302 B1 | 12/2007 | Schuler et al. |
| 7,313,430 B2 | 12/2007 | Urquhart et al. |
| 7,324,851 B1 | 1/2008 | DiLorenzo |
| 7,346,382 B2 | 3/2008 | McIntyre et al. |
| 7,388,974 B2 | 6/2008 | Yanagita |
| 7,437,193 B2 | 10/2008 | Parramon et al. |
| 7,463,928 B2 | 12/2008 | Lee et al. |
| 7,499,048 B2 | 3/2009 | Sieracki et al. |
| 7,505,815 B2 | 3/2009 | Lee et al. |
| 7,526,071 B2 * | 4/2009 | Drapeau .............. A61B 5/0064 378/163 |
| 7,548,786 B2 | 6/2009 | Lee et al. |
| 7,565,199 B2 | 7/2009 | Sheffield et al. |
| 7,603,177 B2 | 10/2009 | Sieracki et al. |
| 7,617,002 B2 | 11/2009 | Goetz |
| 7,623,918 B2 | 11/2009 | Goetz |
| 7,650,184 B2 | 1/2010 | Walter |
| 7,657,319 B2 | 2/2010 | Goetz et al. |
| 7,672,734 B2 | 3/2010 | Anderson et al. |
| 7,676,273 B2 | 3/2010 | Goetz et al. |
| 7,680,526 B2 | 3/2010 | McIntyre et al. |
| 7,734,340 B2 | 6/2010 | De Ridder |
| 7,761,165 B1 | 7/2010 | He et al. |
| 7,826,902 B2 | 11/2010 | Stone et al. |
| 7,848,802 B2 | 12/2010 | Goetz et al. |
| 7,860,548 B2 | 12/2010 | McIntyre et al. |
| 7,904,134 B2 | 3/2011 | McIntyre et al. |
| 7,945,105 B1 | 5/2011 | Jaenisch |
| 7,949,395 B2 | 5/2011 | Kuzma |
| 7,974,706 B2 | 7/2011 | Moffitt et al. |
| 8,019,439 B2 | 9/2011 | Kuzma et al. |
| 8,175,710 B2 | 5/2012 | He |
| 8,180,601 B2 | 5/2012 | Butson et al. |
| 8,195,300 B2 | 6/2012 | Gliner et al. |
| 8,224,450 B2 | 7/2012 | Brase |
| 8,255,060 B2 * | 8/2012 | Goetz ................ A61N 1/36185 607/59 |
| 8,257,684 B2 | 9/2012 | Covalin et al. |
| 8,262,714 B2 | 9/2012 | Hulvershorn et al. |
| 8,364,278 B2 | 1/2013 | Pianca et al. |
| 8,429,174 B2 | 4/2013 | Ramani et al. |
| 8,452,415 B2 | 5/2013 | Goetz et al. |
| 8,543,189 B2 | 9/2013 | Paitel et al. |
| 8,606,360 B2 | 12/2013 | Butson et al. |
| 8,620,452 B2 | 12/2013 | King et al. |
| 8,918,184 B1 | 12/2014 | Torgerson et al. |
| 8,995,731 B2 * | 3/2015 | Joglekar .................. A61B 6/12 382/128 |
| 2001/0031071 A1 | 10/2001 | Nichols et al. |
| 2002/0032375 A1 | 3/2002 | Bauch et al. |
| 2002/0062143 A1 | 5/2002 | Baudino et al. |
| 2002/0087201 A1 | 7/2002 | Firlik et al. |
| 2002/0099295 A1 | 7/2002 | Gil et al. |
| 2002/0115603 A1 | 8/2002 | Whitehouse |
| 2002/0116030 A1 | 8/2002 | Rezei |
| 2002/0123780 A1 | 9/2002 | Grill et al. |
| 2002/0128694 A1 | 9/2002 | Holsheimer |
| 2002/0151939 A1 | 10/2002 | Rezai |
| 2002/0183607 A1 | 12/2002 | Bauch et al. |
| 2002/0183740 A1 | 12/2002 | Edwards et al. |
| 2002/0183817 A1 | 12/2002 | Van Venrooij et al. |
| 2003/0097159 A1 | 5/2003 | Schiff et al. |
| 2003/0149450 A1 | 8/2003 | Mayberg |
| 2003/0171791 A1 | 9/2003 | KenKnight et al. |
| 2003/0212439 A1 | 11/2003 | Schuler et al. |
| 2004/0034394 A1 | 2/2004 | Woods et al. |
| 2004/0044279 A1 | 3/2004 | Lewin et al. |
| 2004/0044378 A1 | 3/2004 | Holsheimer |
| 2004/0044379 A1 | 3/2004 | Holsheimer |
| 2004/0054297 A1 | 3/2004 | Wingeier et al. |
| 2004/0059395 A1 | 3/2004 | North et al. |
| 2004/0106916 A1 | 6/2004 | Quaid et al. |
| 2004/0133248 A1 | 7/2004 | Frei et al. |
| 2004/0152957 A1 | 8/2004 | Stivoric et al. |
| 2004/0181262 A1 | 9/2004 | Bauhahn |
| 2004/0186532 A1 | 9/2004 | Tadlock |
| 2004/0199216 A1 | 10/2004 | Lee et al. |
| 2004/0267330 A1 | 12/2004 | Lee et al. |
| 2005/0021090 A1 | 1/2005 | Schuler et al. |
| 2005/0033380 A1 | 2/2005 | Tanner et al. |
| 2005/0049649 A1 | 3/2005 | Luders et al. |
| 2005/0060001 A1 | 3/2005 | Singhal et al. |
| 2005/0060009 A1 | 3/2005 | Goetz |
| 2005/0070781 A1 | 3/2005 | Dawant et al. |
| 2005/0075689 A1 | 4/2005 | Toy et al. |
| 2005/0085714 A1 | 4/2005 | Foley et al. |
| 2005/0165294 A1 | 7/2005 | Weiss |
| 2005/0171587 A1 | 8/2005 | Daglow et al. |
| 2005/0228250 A1 | 10/2005 | Bitter et al. |
| 2005/0251061 A1 | 11/2005 | Schuler et al. |
| 2005/0261061 A1 | 11/2005 | Nguyen et al. |
| 2005/0261601 A1 | 11/2005 | Schuler et al. |
| 2005/0261747 A1 | 11/2005 | Schuler et al. |
| 2005/0267347 A1 | 12/2005 | Oster |
| 2005/0288732 A1 | 12/2005 | Schuler et al. |
| 2006/0004422 A1 | 1/2006 | De Ridder |
| 2006/0017749 A1 | 1/2006 | McIntyre et al. |
| 2006/0020292 A1 | 1/2006 | Goetz et al. |
| 2006/0069415 A1 | 3/2006 | Cameron et al. |
| 2006/0094951 A1 | 5/2006 | Dean et al. |
| 2006/0095088 A1 | 5/2006 | De Ridder |
| 2006/0155340 A1 | 7/2006 | Schuler et al. |
| 2006/0206169 A1 | 9/2006 | Schuler |
| 2006/0218007 A1 | 9/2006 | Bjorner et al. |
| 2006/0224189 A1 | 10/2006 | Schuler et al. |
| 2006/0235472 A1 | 10/2006 | Goetz et al. |
| 2006/0259079 A1 | 11/2006 | King |
| 2006/0259099 A1 | 11/2006 | Goetz et al. |
| 2007/0000372 A1 | 1/2007 | Rezai et al. |
| 2007/0027514 A1 | 2/2007 | Gerber |
| 2007/0043268 A1 | 2/2007 | Russell |
| 2007/0049817 A1 | 3/2007 | Preiss et al. |

(56) References Cited

U.S. PATENT DOCUMENTS

| | | |
|---|---|---|
| 2007/0067003 A1 | 3/2007 | Sanchez et al. |
| 2007/0078498 A1 | 4/2007 | Rezai et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0135855 A1 | 6/2007 | Foshee et al. |
| 2007/0150036 A1 | 6/2007 | Anderson |
| 2007/0156186 A1 | 7/2007 | Lee et al. |
| 2007/0162086 A1 | 7/2007 | DiLorenzo |
| 2007/0162235 A1 | 7/2007 | Zhan et al. |
| 2007/0168004 A1 | 7/2007 | Walter |
| 2007/0168007 A1 | 7/2007 | Kuzma et al. |
| 2007/0185544 A1 | 8/2007 | Dawant et al. |
| 2007/0191887 A1 | 8/2007 | Schuler et al. |
| 2007/0191912 A1 | 8/2007 | Fischer et al. |
| 2007/0197891 A1 | 8/2007 | Shachar et al. |
| 2007/0203450 A1 | 8/2007 | Berry |
| 2007/0203532 A1 | 8/2007 | Tass et al. |
| 2007/0203537 A1 | 8/2007 | Goetz et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0265664 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0039895 A1 | 2/2008 | Fowler et al. |
| 2008/0071150 A1 | 3/2008 | Miesel et al. |
| 2008/0081982 A1 | 4/2008 | Simon et al. |
| 2008/0086451 A1 | 4/2008 | Torres et al. |
| 2008/0103533 A1 | 5/2008 | Patel et al. |
| 2008/0114233 A1 | 5/2008 | McIntyre et al. |
| 2008/0114579 A1 | 5/2008 | McIntyre et al. |
| 2008/0123922 A1 | 5/2008 | Gielen et al. |
| 2008/0123923 A1 | 5/2008 | Gielen et al. |
| 2008/0133141 A1 | 6/2008 | Frost |
| 2008/0141217 A1 | 6/2008 | Goetz et al. |
| 2008/0154340 A1 | 6/2008 | Goetz et al. |
| 2008/0154341 A1 | 6/2008 | McIntyre et al. |
| 2008/0163097 A1 | 7/2008 | Goetz et al. |
| 2008/0183256 A1 | 7/2008 | Keacher |
| 2008/0188734 A1 | 8/2008 | Suryanarayanan et al. |
| 2008/0215118 A1 | 9/2008 | Goetz et al. |
| 2008/0227139 A1 | 9/2008 | Deisseroth et al. |
| 2008/0242950 A1 | 10/2008 | Jung et al. |
| 2008/0261165 A1 | 10/2008 | Steingart et al. |
| 2008/0269588 A1 | 10/2008 | Csavoy et al. |
| 2008/0269599 A1* | 10/2008 | Csavoy .............. A61B 90/17 600/426 |
| 2008/0300654 A1 | 12/2008 | Lambert et al. |
| 2008/0300797 A1 | 12/2008 | Tabibiazar et al. |
| 2009/0016491 A1 | 1/2009 | Li |
| 2009/0054950 A1 | 2/2009 | Stephens |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0118635 A1 | 5/2009 | Lujan et al. |
| 2009/0118786 A1 | 5/2009 | Meadows et al. |
| 2009/0149917 A1 | 6/2009 | Whitehurst et al. |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0198354 A1 | 8/2009 | Wilson |
| 2009/0204192 A1 | 8/2009 | Carlton et al. |
| 2009/0208073 A1 | 8/2009 | McIntyre et al. |
| 2009/0210208 A1 | 8/2009 | McIntyre et al. |
| 2009/0242399 A1 | 10/2009 | Kamath et al. |
| 2009/0276008 A1 | 11/2009 | Lee et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010566 A1 | 1/2010 | Thacker et al. |
| 2010/0010646 A1 | 1/2010 | Drew et al. |
| 2010/0023103 A1 | 1/2010 | Elborno |
| 2010/0023130 A1 | 1/2010 | Henry et al. |
| 2010/0030312 A1 | 2/2010 | Shen |
| 2010/0049276 A1 | 2/2010 | Blum et al. |
| 2010/0049280 A1 | 2/2010 | Goetz |
| 2010/0064249 A1 | 3/2010 | Groetken |
| 2010/0113959 A1 | 5/2010 | Pascual-Leone et al. |
| 2010/0121409 A1 | 5/2010 | Kothandaraman et al. |
| 2010/0135553 A1 | 6/2010 | Joglekar |
| 2010/0137944 A1 | 6/2010 | Zhu |
| 2010/0152604 A1 | 6/2010 | Kuala et al. |
| 2010/0179562 A1 | 7/2010 | Linker et al. |
| 2010/0324410 A1 | 12/2010 | Paek et al. |
| 2010/0331883 A1 | 12/2010 | Schmitz et al. |
| 2011/0040351 A1 | 2/2011 | Butson et al. |
| 2011/0066407 A1 | 3/2011 | Butson et al. |
| 2011/0172737 A1 | 7/2011 | Davis et al. |
| 2011/0184487 A1 | 7/2011 | Alberts et al. |
| 2011/0191275 A1 | 8/2011 | Lujan et al. |
| 2011/0196253 A1 | 8/2011 | McIntyre et al. |
| 2011/0213440 A1 | 9/2011 | Fowler et al. |
| 2011/0306845 A1 | 12/2011 | Osorio |
| 2011/0306846 A1 | 12/2011 | Osorio |
| 2011/0307032 A1 | 12/2011 | Goetz et al. |
| 2012/0046715 A1 | 2/2012 | Moffitt et al. |
| 2012/0078106 A1 | 3/2012 | Dentinger et al. |
| 2012/0089205 A1 | 4/2012 | Boyden et al. |
| 2012/0116476 A1 | 5/2012 | Kothandaraman |
| 2012/0165898 A1 | 6/2012 | Moffitt |
| 2012/0165901 A1 | 6/2012 | Zhu et al. |
| 2012/0207378 A1 | 8/2012 | Gupta et al. |
| 2012/0226138 A1 | 9/2012 | DeSalles et al. |
| 2012/0229468 A1 | 9/2012 | Lee et al. |
| 2012/0265262 A1 | 10/2012 | Osorio |
| 2012/0265268 A1 | 10/2012 | Blum et al. |
| 2012/0302912 A1 | 11/2012 | Moffitt et al. |
| 2012/0303087 A1 | 11/2012 | Moffitt et al. |
| 2012/0314924 A1 | 12/2012 | Carlton et al. |
| 2012/0316619 A1 | 12/2012 | Goetz et al. |
| 2013/0039550 A1 | 2/2013 | Blum et al. |
| 2013/0060305 A1 | 3/2013 | Bokil |
| 2013/0116748 A1 | 5/2013 | Bokil et al. |
| 2013/0116749 A1 | 5/2013 | Carlton et al. |
| 2013/0116929 A1 | 5/2013 | Carlton et al. |
| 2014/0067018 A1 | 3/2014 | Carcieri et al. |
| 2014/0277284 A1 | 9/2014 | Chen et al. |
| 2015/0134031 A1 | 5/2015 | Moffitt et al. |

FOREIGN PATENT DOCUMENTS

| | | |
|---|---|---|
| EP | 1372780 | 1/2004 |
| EP | 1559369 | 8/2005 |
| WO | 97/39797 | 10/1997 |
| WO | 98/48880 | 11/1998 |
| WO | 2001/090876 A1 | 11/2001 |
| WO | 02/26314 | 4/2002 |
| WO | 02/28473 | 4/2002 |
| WO | 02/065896 | 8/2002 |
| WO | 02/072192 | 9/2002 |
| WO | 03/086185 | 10/2003 |
| WO | 2004/019799 A2 | 3/2004 |
| WO | 2004041080 | 5/2005 |
| WO | 2006017053 | 2/2006 |

(56) References Cited

FOREIGN PATENT DOCUMENTS

| WO | 2006113305 | 10/2006 |
| --- | --- | --- |
| WO | 2007/097859 A1 | 8/2007 |
| WO | 2007/097861 A1 | 8/2007 |
| WO | 2007/100427 A1 | 9/2007 |
| WO | 2007/100428 A1 | 9/2007 |
| WO | 2007/112061 A2 | 10/2007 |
| WO | 2009097224 A1 | 8/2009 |
| WO | 2010/120823 A2 | 10/2010 |
| WO | 2011025865 | 3/2011 |
| WO | 2011/139779 A1 | 11/2011 |
| WO | 2011/159688 A2 | 12/2011 |
| WO | 2012088482 | 6/2012 |

OTHER PUBLICATIONS

Obeso, J. A., et al., "Deep-brain stimulation of the subthalamic nucleus or the pars interna of the globus pallidus in Parkinson's disease.", N Engl J Med., 345{13I. The Deep-Brain Stimulation for Parkinson's Disease Study Group, (Sep. 27, 2001 ),956-63.

Fisekovic et al., "New Controller for Functional Electrical Stimulation Systems", Med. Eng. Phys. 2001; 23:391-399.

Patrick, S. K., et al., "Quantification of the UPDRS rigidity scale", IEEE Transactions on Neural Systems and Rehabilitation Engineering, [see also IEEE Trans. on Rehabilitation Engineering 9(1). (2001), 31-41.

Phillips, M. D., et al., "Parkinson disease: pattern of functional MR imaging activation during deep brain stimulation of subthalamic nucleus—initial experience", Radiology 239(1). (Apr. 2006),209-16.

Merrill, D. R., et al., "Electrical stimulation of excitable tissue: design of efficacious and safe protocols", J Neurosci Methods. 141(2), (Feb. 15, 2005), 171-98.

Montgomery, E. B., et al., "Mechanisms of deep brain stimulation and future technical developments.", Neurol Res. 22(3), (Apr. 2000),259-66.

Moss, J. , et al., "Electron microscopy of tissue adherent to explanted electrodes in dystonia and Parkinson's disease", Brain, 127{Pt 12). (Dec. 2004),2755-63.

Hunka, K. et al., Nursing Time to Program and Assess Deep Brain Stimulators in Movement Disorder Pateints, J. Neursci Nurs. 37: 204-10 (Aug. 2005).

Miocinovic S., et al., "Sensitivity of temporal excitation properties to the neuronal element activated by extracellular stimulation", J Neurosci Methods. 132(1). (Jan. 15, 2004), 91-9.

McIntyre, C. C. et al., "How does deep brain stimulation work? Present understanding and future questions.", J Clin Neurophysiol. 21(1). (Jan.-Feb. 2004 ), 40-50.

Grill, W. M., "Stimulus waveforms for selective neural stimulation", IEEE Engineering in Medicine and Biology Magazine, 14{4}, (Jul.-Aug. 1995), 375-385.

Plaha, P. , et al., "Stimulation of the caudal zona incerta is superior to stimulation of the subthalamic nucleus in improving contralateral parkinsonism.", Brain 129{Pt 7) (Jul. 2006), 1732-4 7.

Rattay, F, "Analysis of models for external stimulation of axons", IEEE Trans. Biomed. Eng. vol. 33 (1986),974-977.

Rattay, F., "Analysis of the electrical excitation of CNS neurons", IEEE Transactions on Biomedical Engineering 45 (6). (Jun. 1998),766-772.

Rose, T. L., et al., "Electrical stimulation with Pt electrodes. VIII. Electrochemically safe charge injection limits with 0.2 ms pulses [neuronal application]", IEEE Transactions on Biomedical Engineering, 37(11 }, (Nov. 1990), 1118-1120.

Rubinstein, J. T., et al., "Signal coding in cochlear implants: exploiting stochastic effects of electrical stimulation", Ann Otol Rhinol Laryngol Suppl., 191, (Sep. 2003), 14-9.

Schwan. H.P., et al., "The conductivity of living tissues.", Ann NY Acad Sci., 65(6). (Aug. 1957), 1007-13.

Taylor, R. S., et al., "Spinal cord stimuation for chronic back and leg pain and failed back surgery syndrome: a systematic review and analysis of prognostic factors", Spine 30(1). (Jan. 1, 2005), 152-60.

Micheli-Tzanakou, E., et al., "Computational Intelligence for target assesment in Parkinson's disease", Proceedings of SPIE vol. 4479. Applications and Science of Neural Networks. Fuzzy Systems, and Evolutionary Computation IV,(2001),54-69.

Hodaie, M., et al., "Chronic anterior thalamus stimuation for intractable epilepsy." Epilepsia, 43(6) (Jun. 2002), pp. 603-608.

Geddes. L. A., et al., "The specific resistance of biological material—a compendium of data for the biomedical engineer and physiologist.", Med Biol Ena. 5(3), (May 1967),271-93.

Gimsa, J., et al., "Choosing electrodes for deep brain stimulation experiments—electrochemical considerations.", J Neurosci Methods, 142(2), (Mar. 30, 2005),251-65.

Vidailhet, M. , et al., "Bilateral deep-brain stimulation of the globus pallidus in primary generalized dystonia", N Engl J Med. 352(5) (Feb. 3, 2005),459-67.

Viola, P., et al., "Alignment by maximization of mutual information", International Journal of Com outer Vision 24(2). ( 1997), 137-154.

Volkmann, J. , et al., "Basic algorithms for the programming of deep brain stimulation in Parkinson's disease", Mov Disord., 21 Suppl 14. (Jun. 2006),S284-9.

Walter, B. L., et al. "Surgical treatment for Parkinson's disease". Lancet Neural. 3(12). (Dec. 2004),719-28.

Wei, X. F., et al., "Current density distributions, field distributions and impedance analysis of segmented deep brain stimulation electrodes", J Neural Eng . . . 2(4). (Dec. 2005), 139-47.

Zonenshayn, M. , et al., "Location of the active contact within the subthalamic nucleus (STN) in the treatment of idiopathic Parkinson's disease.", Surg Neurol., 62(3) (Sep. 2004),216-25.

Da Silva et al (A primer on diffusion tensor imaging of anatomical substructures. Neurosurg Focus 15(1): p. 1-4, Article 4, 2003.).

Mcintyre, Cameron C., et al., "Uncovering the mechanisms of deep brain stimulation for Parkinson's disease through functional imaging, neural recording, and neural modeling," Crit Rev Biomed Eng., 30(4-6) (2002), pp. 249-281.

Mcintyre, Cameron C., et al., "Uncovering the mechanism(s) of action of deep brain stimulation: activation, inhibition, or both," Clin Neurophysiol, 115(6) (Jun. 2004), pp. 1239-1248.

Mcintyre, C. C., et al., "Sensitivity analysis of a model of mammalian neural membrane," Biol Cybern., 79(1) (Jul. 1998), pp. 29-37.

Mcintyre, Cameron C., et al., "Selective microstimulation of central nervous system neurons," Annals of biomedical engineering, 28(3) (Mar. 2000), pp. 219-233.

Mcintyre, Cameron C., et al., "Modeling the excitability of mammalian nerve fibers: influence of aflerpotentials on the recovery cycle," J Neurophysiol, 87(2) (Feb. 2002), pp. 995-1006.

Mcintyre, C. C., et al., Model-based design of stimulus waveforms for selective microstimulation in the central nervous system,, Proceedings of the First Joint [Engineering in Medicine and Biology, 1999. 21st Annual Conf. and the 1999 Annual FallMeeting of the Biomedical Engineering Soc.] BM ES/EMBS Conference, vol. 1 (1999), p. 384.

Mcintyre, C. C., et al., "Model-based design of stimulus trains for selective microstimulation of targeted neuronal populations," Proceedings of the 23rd Annual International Conference of the IEEE Engineering in Medicine and Biology Society, vol. 1 (2001), pp. 806-809.

Mcintyre, Cameron C., et al., "Model-based Analysis of deep brain stimulation of the thalamus," Proceedings of the Second joint EMBS/BM ES Conference, vol. 3, Annual Fall Meeting of the Biomedical Engineering Society (Cal. No. 02CH37392) IEEEPiscataway, NJ (2002), pp. 2047-2048.

Mcintyre, C. C., et al., "Microstimulation of spinal motoneurons: a model study," Proceedings of the 19th Annual International Conference of the IEEE Engineering in Medicine and Biology society, vol. 5, (1997), pp. 2032-2034.

Mcintyre, C. C., et al., "Extracellular stimulation of central neurons: influence of stimulus waveform and frequency on neuronal output," J. Neurophysiol., 88(4), (Oct. 2002), pp. 1592-1604.

(56) References Cited

OTHER PUBLICATIONS

Liu, Haiying, et al., "Intra-operative MR-guided DBS implantation for treating PD and ET," Proceedings of SPIE vol. 4319, Department of Radiology & Neurosurgery, University of Minnesota, Minneapolis, MN 55455 (2001), pp. 272-276.
Levy, Al., et al., "An Internet-connected, patient-specific, deformable brain atlas integrated into a surgical navigation system," J Digit Imaging, 10(3 Suppl 1) (Aug. 1997), pp. 231-237.
Lee, D. C., et al., "Extracellular electrical stimulation of central neurons: quantitative studies," In: Handbook of neuroprosthetic methods, WE Finn and PG Lopresti (eds) CRC Press (2003), pp. 95-125.
Le Bihan, D., et al., "Diffusion tensor imaging: concepts and applications," J Magn Reson Imaging, 13(4) (Apr. 2001), pp. 534-546.
Krack, P., et al., "Postoperative management of subthalamic nucleus stimulation for Parkinson's disease," Mov. Disord., vol. 17(suppl 3) (2002), pp. 188-197.
Jones, DK., et al., "Optimal strategies for measuring diffusion in anisotropic systems by magnetic resonance imaging," Magn. Reson. Med., 42(3) (Sep. 1999), pp. 515-525.
Jezernik, S., et al., "Neural network classification of nerve activity recorded in a mixed nerve," Neurol Res., 23(5) (Jul. 2001), pp. 429-434.
Holsheimer, J., et al., "Identification of the target neuronal elements in electrical deep brain stimulation," Eur J Neurosci., 12(12) (Dec. 2000), pp. 4573-4577.
Hoekema, R., et al., "Multigrid solution of the potential field in modeling electrical nerve stimulation," Comput Biomed Res., 31(5) (Oct. 1998), pp. 348-362.
Saxena, et al., "Cerebral glucose metabolism in obsessive-compulsive hoarding," Am J Psychiatry. 161 (6) (2004), pp. 1038-1048.
Zhang, Y., et al., "Atlas-guided tract reconstruction for automated and comprehensive examination of the white matter anatomy," Neuroimage 52(4) (2010), pp. 1289-1301.
""BioPSE" The Biomedical Problem Solving Environment", htt12://www.sci.utah.edu/cibc/software/index.html, MCRR Center for Integrative Biomedical Computing,(2004).
Andrews, R. J., "Neuroprotection trek—the next generation: neuromodulation I. Techniques—deep brain stimulation, vagus nerve stimulation, and transcranial magnetic stimulation.", Ann NY Acad Sci. 993. (May 2003),1-13.
Machado. et al., "Functional topography of the ventral striatum and anterior limb of the internal capsule determined by electrical stimulation of awake patients," Clin Neurophysiol 120 (11) (2009), pp. 1941-1948.
Lujan, J.L. et al., "Automated 3-Dimensional Brain Atlas Fitting to Microelectrode Recordings from Deep Brain Stimulation Surgeries," Stereotact. Fune!. Neurosurg. 87(2009), pp. 229-240.
Lujan, et al., "Tracking the mechanisms of deep brain stimulation for neuropsychiatric disorders." Front Biosci 13 (2008), pp. 5892-5904.
Lozano, et al., "Subcallosal cingulate gyrus deep brain stimulation for treatment-resistant depression." Biol Psychiatry 64 (6) (2008), pp. 461-467.
Kopell, et al., "Deep brain stimulation for psychiatric disorders," J Clin Neurophysiol 21 (1) (2004), pp. 51-67.
Johansen-Berg, et al., "Anatomical connectivity of the subgenual cingulate region targeted with deep brain stimulation for treatment-resistant depression," Cereb Cortex 18 (6) (2008), pp. 1374-1383.
Hua, et al., "Tract probability maps in stereotaxic spaces analyses of white matter anatomy and tract-specific quantification," Neuroimage 39 (1) (2008), pp. 336-347.
McIntyre,C. C., et al., "Network perspectives on the mechanisms of deep brain stimulation," Neurobiol Dis 38 (3) (2010), pp. 329-337.
Andrews, R. J., "Neuroprotection trek—the next generation: neuromodulation II. Applications—epilepsy, nerve regeneration, neurotrophins.", Ann NY Acad Sci. 993 (May 2003), 14-24.

Astrom, M. , et al., "The effect of cystic cavities on deep brain stimulation in the basal ganglia: a simulation-based study", J Neural Eng., 3(2), (Jun. 2006).132-8.
Mouine et al. "Multi-Strategy and Multi-Algorithm Cochlear Prostheses", Biomed. Sci. Instrument, 2000; 36:233-238.
Back, C. , et al., "Postoperative Monitoring of the Electrical Properties of Tissue and Electrodes in Deep Brain Stimulation", Neuromodulation, 6(4), (Oct. 2003 ),248-253.
Baker, K. B., et al., "Evaluation of specific absorption rate as a dosimeter of MRI-related implant heating", J Magn Reson Imaging., 20(2), (Aug. 2004),315-20.
Brown, J. "Motor Cortex Stimulation," Neurosurgical Focus ( Sep. 15, 2001) 11(3):E5.
Budai et al., "Endogenous Opioid Peptides Acting at m-Opioid Receptors in the Dorsal Horn Contribute to Midbrain Modulation of Spinal Nociceptive Neurons," Journal of Neurophysiology (1998) 79(2): 677-687.
Cesselin, F. "Opioid and anti-opioid peptides," Fundamental and Clinical Pharmacology (1995) 9(5): 409-33 (Abstact only).
Rezai et al., "Deep Brain Stimuation for Chronic Pain" Surgical Management of Pain, Chapter 44 pp. 565-576 (2002).
Xu, MD., Shi-Ang, article entitled "Comparison of Half-Band and Full-Band Electrodes for Intracochlear Electrical Stimulation", Annals of Otology, Rhinology & Laryngology (Annals of Head & Neck Medicine & Surgery), vol. 102 (5) pp. 363-367 May 1993.
Bedard, C. , et al., "Modeling extracellular field potentials and the frequency-filtering properties of extracellular space", Biophys J . . . 86(3). (Mar. 2004) 1829-42.
Benabid, A. L., et al., "Future prospects of brain stimulation", Neurol Res.;22(3), (Apr. 2000),237-46.
Brummer, S. B., et al., "Electrical Stimulation with Pt Electrodes: II—Estimation of Maximum Surface Redox (Theoretical Non-Gassing) Limits", IEEE Transactions on Biomedical Engineering, vol. BME-24, Issue 5, (Sep. 1977),440-443.
Butson, Christopher R., et al., "Deep Brain Stimulation of the Subthalamic Nucleus: Model-Based Analysis of the Effects of Electrode Capacitance on the Volume of Activation", Proceedings of the 2nd International IEEE EMBS, (Mar. 16-19, 2005),196-197.
Mcintyre, Cameron C., et al., "Cellular effects of deep brain stimulation: model-based analysis of activation and inhibition," J Neurophysiol, 91(4) (Apr. 2004), pp. 1457-1469.
Chaturvedi, A., et al., "Subthalamic Nucleus Deep Brain Stimulation: Accurate Axonal Threshold Prediction with Diffusion Tensor Based Electric Field Models", Engineering in Medicine and Biology Society, 2006. EMBS' 06 28th Annual International Conference of the IEEE, IEEE, Piscataway, NJ USA, Aug. 30, 2006.
Butson, Christopher et al., "Predicting the Effects of Deep Brain Stimulation with Diffusion Tensor Based Electric Field Models" Jan. 1, 2001, Medical Image Computing and Computer-Assisted Intervention-Mic CAI 2006 Lecture Notes in Computer Science, LNCS, Springer, Berlin, DE.
Butson, C. R., et al., "Deep brainstimulation interactive visualization system", Society for Neuroscience vol. 898.7 (2005).
Grill, WM., et al., "Electrical properties of implant encapsulation tissue", Ann Biomed Eng. vol. 22. (1994),23-33.
McNaughtan et al., "Electrochemical Issues in Impedance Tomography", 1st World Congress on Industrial Process Tomography, Buxton, Greater Manchester, Apr. 14-17, 1999.
Hardman, C. D., et al., "Comparison of the basal ganglia in rats, marmosets, macaques, baboons, and humans: volume and neuronal number for the output, internal relay, and striatal modulating nuclei", J Comp Neurol., 445(3). (Apr. 8, 2002):238-55.
Hashimoto, T. , et al., "Stimulation of the subthalamic nucleus changes the firing pattern of pallidal neurons", J Neurosci. 23(5). (Mar. 1, 2003), 1916-23.
Haslinger, B., et al., "Frequency-correlated decreases of motor cortex activity associated with subthalamic nucleus stimulation in Parkinson's disease.", Neuroimage 28(3). (Nov. 15, 2005),598-606.
Haueisen, J, et al., "The influence of brain tissue anisotropy on human EEG and MEG", Neuroimage 15(1) (Jan. 2002),159-166.

(56) References Cited

OTHER PUBLICATIONS

Hemm, S., et al., "Deep brain stimulation in movement disorders: stereotactic coregistration of two-dimensional electrical field modeling and magnetic resonance imaging.", J Neurosurg. 103(6): (Dec. 2005),949-55.
Hemm, S., et al., "Evolution of Brain Impedance in Dystonic Patients Treated by GPi Electrical Stimulation", Neuromodulation 7(2) (Apr. 2004),67-75.
Hershey, T., et al., "Cortical and subcortical blood flow effects of subthalamic nucleus stimulation in PD.". Neurology 61(6). (Sep. 23, 2003),816-21.
Herzog, J., et al., "Most effective stimulation site in subthalamic deep brain stimulation for Parkinson's disease", Mov Disord. 19(9). (Sep. 2004),1050-4.
Hines, M. L., et al., "The NEURON simulation environment". Neural Comput. 9(6). (Aug. 15. 1997), 1179-209.
Holsheimer, J., et al., "Chronaxie calculated from current-duration and voltage-duration data", J Neurosci Methods. 97(1). (Apr. 1, 2000),45-50.
Johnson, M. D., et al., "Repeated voltage biasing improves unit recordings by reducing resistive tissue impedances", IEEE Transactions on Neural Systems and Rehabilitation Engineering, [see also IEEE Trans. on Rehabilitation Engineering (2005), 160-165.
Kitagawa, M., et al., "Two-year follow-up of chronic stimulation of the posterior subthalamic white matter for tremor-dominant Parkinson's disease.", Neurosurgery. 56(2). (Feb. 2005),281-9.
Limousin, P., et al., "Electrical stimulation of the subthalamic nucleus in advanced Parkinson's disease", N Engl J Med . . . 339(16), (Oct. 15, 1998). 1105-11.
Foster, K. R., et al., "Dielectric properties of tissues and biological materials: a critical review.", Grit Rev Biomed Ena. 17( 1 ). {1989),25-104.
McIntyre; Cameron , et al.; "Finite element analysis of the current-density and electric field generated by metal microelectrodes", Ann Biomed Eng . 29(3), (2001 ),227-235.
Mayr et al., "Basic Design and Construction of the Vienna FES Implants: Existing Solutions and Prospects for New Generations of Implants"; Medical Engineering & Physics; 2001; 23:53-60.
Wakana, S., et al., "Reproducibility of quantitative tractography methods applied to cerebral white matter," Neuroimage 36 (3) (2007), pp. 630-644.
Viola, et al.; "Importance-driven focus of attention," IEEE Trans Vis Comput Graph 12 (5) (2006), pp. 933-940.
Malone, et al., "Deep brain stimulation of the ventral capsule/ventral striatum for treatment-resistant depression." Biol Psychiatry 65 (4) (2009), pp. 267-275.
Mcintyre, Cameron C., et al., "Electric Field and Stimulating Influence generated by Deep Brain Stimulation of the Subthalamaic Nucleus," Clinical Neurophysiology, 115(3) (Mar. 2004), pp. 589-595.
Mcintyre, Cameron C., et al., "Electric field generated by deep brain stimulation of the subthalamic nucleus," Biomedical Engineering Society Annual Meeting, Nashville TN (Oct. 2003), 16 pages.
Mcintyre, Cameron C., et al., "Excitation of central nervous system neurons by nonuniform electric fields," Biophys. J., 76(2) (1999), pp. 878-888.
McNeal, DR., et al. "Analysis of a model for excitation of myelinated nerve," IEEE Trans Biomed Eng., vol. 23 (1976), pp. 329-337.
Micheli-Tzanakou, E., et al., "Computational Intelligence for target assesment in Parkinson's disease," Proceedings of SPIE vol. 4479, Applications and Science of Neural Networks, Fuzzy Systems, and Evolutionary Computation IV (2001 ), pp. 54-69.
Miocinovic, S., et al., "Computational analysis of subthalamic nucleus and lenticular fasciculus activation during therapeutic deep brain stimulation," J Neurophysiol., 96(3) (Sep. 2006), pp. 1569-1580.
Miranda, P. C., et al., "The distribution of currents inducedin the brain by Magnetic Stimulation: a finite element analysis incorporating OT-MRI-derived conductivity data," Proc. Intl. Soc. Mag. Reson. Med. 9 (2001 ), p. 1540.
Miranda, P. C., et al., "The Electric Field Induced in the Brain by Magnetic Stimulation: A 3-D Finite-Element Analysis of the Effect of Tissue Heterogeneity and Anisotropy," IEEE Transactions on Biomedical Enginering, 50(9) (Sep. 2003), pp. 1074-1085.
Moffitt, MA., et al., "Prediction of myelinated nerve fiber stimulation thresholds: limitations of linear models," IEEE Transactions on Biomedical Engineering, 51 (2) (2003), pp. 229-236.
Moro, E. et al., "The impact on Parkinson's disease of electrical parameter settings in STN stimulation," Neurology 59 (5) (Sep. 10, 2002), pp. 706-713.
Nowak, LG., et al., "Axons, but not cell bodies, are activated by electrical stimulation in cortical gray matter. I. Evidence from chronaxie measurements," Exp. Brain Res., 118(4) (Feb. 1998), pp. 477-488.
Nowak, LG., et al., "Axons, but not cell bodies, are activated by electrical stimulation in cortical gray matter. II. Evidence from selective inactivation of cell bodies and axon initial segments," Exp. Brain Res., 118(4) (Feb. 1998), pp. 489-500.
O'Suilleabhain, PE., et al., "Tremor response to polarity, voltage, pulsewidth and frequency of thalamic stimulation," Neurology, 60(5) (Mar. 11, 2003), pp. 786-790.
Pierpaoli, C., et al., "Toward a quantitative assessment of diffusion anisotropy," Magn Reson Med., 36(6) (Dec. 1996), pp. 893-906.
Plonsey, R., et al., "Considerations of quasi-stationarity in electrophysiological systems," Bull Math Biophys., 29(4) (Dec. 1967), pp. 657-664.
Ranck, J B., "Specific impedance of rabbit cerebral cortex," Exp. Neurol., vol. 7 (Feb. 1963), pp. 144-152.
Ranck, J B., et al., "The Specific impedance of the dorsal columns of the cat: an anisotropic medium," Exp. Neurol., 11 (Apr. 1965), pp. 451-463.
Ranck, J B., "Which elements are excited in electrical stimulation of mammalian central nervous system: a review," Brain Res., 98(3) (Nov. 21, 1975), pp. 417-440.
Rattay, F., et al., "A model of the electrically excited human cochlear neuron. I. Contribution of neural substructures to the generation and propagation of spikes," Hear Res., 153(1-2) (Mar. 2001), pp. 43-63.
Rattay, F., "A model of the electrically excited human cochlear neuron. II. Influence of the three-dimensional cochlear structure on neural excitability," Hear Res., 153(1-2) (Mar. 2001), pp. 64-79.
Rattay, F., "Arrival at Functional Electrostimulation by modelling of fiber excitation," Proceedings of the Ninth annual Conference of the IEEE Engineering in Medicine and Biology Society (1987), pp. 1459-1460.
Rattay, F., "The influence of intrinsic noise can preserve the temporal fine structure of speech signals in models of electrically stimulated human cochlear neurones," Journal of Physiology, Scientific Meeting of the Physiological Society. London, England, UK Apr. 19-21, 1999 (Jul. 1999), p. 170P.
Rizzone, M., et al., "Deep brain stimulation of the subthalamic nucleus in Parkinson's disease: effects of variation in stimulation parameters," J. Neurol. Neurosurg. Psychiatry., 71(2) (Aug. 2001), pp. 215-219.
Saint-Cyr, J. A., et al., "Localization of clinically effective stimulating electrodes in the human subthalamic nucleus on magnetic resonance imaging," J. Neurosurg., 87(5) (Nov. 2002), pp. 1152-1166.
Sances, A., et al., "In Electroanesthesia: Biomedical and Biophysical Studies," A Sances and SJ Larson, Eds., Academic Press, NY (1975), pp. 114-124.
SI. Jean, P., et al., "Automated atlas integration and interactive three-dimensional visualization tools for planning and guidance in functional neurosurgery," IEEE Transactions on Medical Imaging, 17(5) (1998), pp. 672-680.
Starr, P.A., et al., "Implantation of deep brain stimulators into the subthalamic nucleus: technical approach and magnetic resonance imaging-verified lead locations," J. Neurosurg., 97(2) (Aug. 2002), pp. 370-387.

(56) References Cited

OTHER PUBLICATIONS

Sterio, D., et al., "Neurophysiological refinement of subthalamic nucleus targeting," Neurosurgery, 50(1) (Jan. 2002), pp. 58-69.
Struijk, J. J., et al., "Excitation of dorsal root fibers in spinal cord stimulation: a theoretical study," IEEE Transactions on Biomedical Engineering, 40(7) (Jul. 1993), pp. 632-639.
Struijk, J J., et al., "Recruitment of dorsal column fibers in spinal cord stimulation influence of collateral branching," IEEE Transactions on Biomedical Engineering, 39(9) (Sep. 1992), pp. 903-912.
Tamma, F., et al., "Anatomo-clinical correlation of intraoperative stimulation-induced side-effects during HF-DBS of the subthalamic nucleus," Neurol Sci., vol. 23 (Suppl 2) (2002), pp. 109-110.
Tarler, M., et al., "Comparison between monopolar and tripolar configurations in chronically implanted nerve cuff electrodes," IEEE 17th Annual Conference Engineering in Medicine and Biology Society, vol. 2 (1995), pp. 1093-109.
Testerman, Roy L., "Coritical response to callosal stimulation: A model for determining safe and efficient stimulus parameters," Annals of Biomedical Engineering, 6(4) (1978), pp. 438-452.
Tuch, D.S., et al., "Conductivity mapping of biological tissue using diffusion MRI," Ann NY Acad Sci., 888 (Oct. 30, 1999), pp. 314-316.
Tuch, D.S., et al., "Conductivity tensor mapping of the human brain using diffusion tensor MRI," Proc Nall Acad Sci USA, 98(20) (Sep. 25, 2001), pp. 11697-11701.
Veraart, C., et al., "Selective control of muscle activation with a multipolar nerve cuff electrode," IEEE Transactions on Biomedical Engineering, 40(7) (Jul. 1993), pp. 640-653.
Vercueil, L., et al., "Deep brain stimulation in the treatment of severe dystonia," J. Neurol., 248(8) (Aug. 2001 ), pp. 695-700.
Vilalte, "Circuit Design of the Power-on-Reset," Apr. 2000, pp. 1-25.
Vitek, J. L., "Mechanisms of deep brain stimulation: excitation or inhibition," Mov. Disord., vol. 17 (Suppl. 3) (2002), pp. 69-72.
Voges, J., et al., "Bilateral high-frequency stimulation in the subthalamic nucleus for the treatment of Parkinson disease: correlation of therapeutic effect with anatomical electrode position," J. Neurosurg., 96(2) (Feb. 2002), pp. 269-279.
Wakana, S., et al., "Fiber tract-based atlas of human white matter anatomy," Radiology. 230(1) (Jan. 2004). pp. 77-87.
Alexander, DC., et al., "Spatial transformations of diffusion tensor magnetic resonance images," IEEE Transactions on Medical Imaging, 20 (11), (2001), pp. 1131-1139.
Wu, Y. R., et al., "Does Stimulation of the GPi control dyskinesia by activating inhibitory axons?," Mov. Disord., vol. 16 (2001), pp. 208-216.
Yelnik, J., et al., "Localization of stimulating electrodes in patients with Parkinson disease by using a three-dimensional atlas-magnetic resonance imaging coregistration method," J Neurosurg., 99(1) (Jul. 2003), pp. 89-99.
Yianni, John, et al., "Globus pallidus internus deep brain stimulation for dystonic conditions: a prospective audit," Mov. Disord., vol. 18 (2003), pp. 436-442.
Zonenshayn, M., et al., "Comparison of anatomic and neurophysiological methods for subthalamic nucleus targeting," Neurosurgery, 47(2) (Aug. 2000), pp. 282-294.
Voghell et al., "Programmable Current Source Dedicated to Implantable Microstimulators" ICM '98 Proceedings of the Tenth International Conference, pp. 67-70.
Grill, W. M., et al., "Deep brain stimulation creates an informational lesion of the stimulated nucleus", Neuroreport. 15I7t (May 19, 2004 ), 1137-40.
Adler, DE., et al., "The tentorial notch: anatomical variation, morphometric analysis, and classification in 100 human autopsy cases," J. Neurosurg., 96(6), (Jun. 2002), pp. 1103-1112.
Jones et al., "An Advanced Demultiplexing System for Physiological Stimulation", IEEE Transactions on Biomedical Engineering, vol. 44 No. 12 Dec. 1997, pp. 1210-1220.

Alo, K. M., et al., "New trends in neuromodulation for the management of neuropathic pain," Neurosurgery, 50(4), (Apr. 2002), pp. 690-703, discussion pp. 703-704.
Ashby, P., et al., "Neurophysiological effects of stimulation through electrodes in the human subthalamic nucleus," Brain, 122 (PI 10), (Oct. 1999), pp. 1919-1931.
Baker, K. B., et al., "Subthalamic nucleus deep brain stimulus evoked potentials: Physiological and therapeutic implications," Movement Disorders, 17(5), (Sep./Oct. 2002), pp. 969-983.
Bammer, R, et al., "Diffusion tensor imaging using single-shot SENSE-EPI", Magn Reson Med., 48(1 ), (Jul. 2002), pp. 128-136.
Basser, P. J., et al., "MR diffusion tensor spectroscopy and imaging," Biophys J., 66(1 ), (Jan. 1994), pp. 259-267.
Basser, P. J., et al., "New currents in electrical stimulation of excitable tissues," Annu Rev Biomed Eng., 2, (2000), pp. 377-397.
Benabid, AL., et al., "Chronic electrical stimulation of the ventralis intermedius nucleus of the thalamus as a treatment of movement disorders," J. Neurosurg., 84(2), (Feb. 1996), pp. 203-214.
Benabid, AL., et al., "Combined (thalamotoy and stimuation) stereotactic surgery of the VIM thalamic nucleus for bilateral Parkinson disease," Appl Neurophysiol, vol. 50, (1987), pp. 344-346.
Benabid, A L., et al., "Long-term suppression of tremor by chronic stimulation of the ventral intermediate thalamic nucleus," Lancet, 337 (8738), (Feb. 16, 1991 ), pp. 403-406.
Nuttin, et al., "Electrical stimulation in anterior limbs of internal capsules in patients with obsessive-compulsive disorder," Lancet 354 (9189) (1999), p. 1526.
Christensen, Gary E., et al., "Volumetric transformation of brain anatomy," IEEE Transactions on Medical Imaging, 16 (6), (Dec. 1997), pp. 864-877.
Cooper, S , et al., "Differential effects of thalamic stimulation parameters on tremor and paresthesias in essential tremor," Movement Disorders, 17(Supp. 5), (2002), p. S193.
Coubes, P, et al., "Treatment of DYT1-generalised dystonia by stimulation of the internal globus pallidus," Lancet, 355 (9222), (Jun. 24, 2000), pp. 2220-2221.
Miocinovic, S., et al., "Experimental and theoretical characterization of the voltage distribution generated by deep brain stimulation," Exp Neurol 216 (i) (2009), pp. 166-176.
Dawant, B. M., et al., "Compuerized atlas-guided positioning of deep brain stimulators: a feasibility study," Biomedical Image registration; Second International Workshop, WBIR 2003, Revised Papers (Lecture notes in Comput. Sci. vol. (2717), Springer-Verlag Berlin, Germany(2003), pp. 142-150.
Finnis, K. W., et al., "3-D functional atalas of subcortical structures for image guided stereotactic neurosurgery," Neuroimage, vol. 9, No. 6, Iss. 2 (1999), p. S206.
Finnis, K. W., et al., "3D Functional Database of Subcorticol Structures for Surgical Guidance in Image Guided Stereotactic Neurosurgery," Medical Image Computing and Computer-Assisted Intervention—MICCAI'99, Second International Conference.Cambridge, UK, Sep. 19-22, 1999, Proceedings (1999), pp. 758-767.
Finnis, K. W., et al., "A 3-Dimensional Database of Deep Brain Functional Anatomy, and Its Application to Image-Guided Neurosurgery," Proceedings of the Third International Conference on Medical Image Computing and Computer-Assisted Intervention. Lecture Notes in Computer Science; vol. 1935 (2000), pp. 1-8.
Finnis, K. W., et al., "A functional database for guidance of surgical and therapeutic procedures in the deep brain," Proceedings of the 22nd Annual International Conference of the IEEE Engineering in Medicine and Biology Society, vol. 3 (2000), pp. 1787-1789.
Finnis, K. W., et al., "Application of a Population Based Electrophysiological Database to the Planning and Guidance of Deep Brain Stereotactic Neurosurgery," Proceedings of the 5th International Conference on Medical Image Computing and Computer-Assisted Intervention-Part 11, Lecture Notes in Computer Science, vol. 2489 (2002), pp. 69-76.
Finnis, K. W., et al., "Subcortical physiology deformed into a patient-specific brain atlas for image-guided stereotaxy," Proceedings of SPIE—vol. 4681 Medical Imaging 2002: Visualization, Image-Guided Procedures, and Display (May 2002), pp. 184-195.

(56) References Cited

OTHER PUBLICATIONS

Finnis, Krik W., et al., "Three-Dimensional Database of Subcortical Electrophysiology for Image-Guided Stereotatic Functional Neurosurgery," IEEE Transactions on Medical Imaging, 22(1) (Jan. 2003), pp. 93-104.
Gabriels, L , et al., "Deep brain stimulation for treatment-refractory obsessive-compulsive disorder: psychopathological and neuropsychological outcome in three cases," Acta Psychiatr Scand., 107(4) (2003), pp. 275-282.
Gabriels, LA., et al., "Long-term electrical capsular stimulation in patients with obsessive-compulsive disorder," Neurosurgery, 52(6) (Jun. 2003), pp. 1263-1276.
Goodall, E. V., et al., "Modeling study of activation and propagation delays during stimulation of peripheral nerve fibers with a tripolar cuff electrode," IEEE Transactions on Rehabilitation Engineering, [see also IEEE Trans. on Neural Systems and Rehabilitation], 3(3) (Sep. 1995), pp. 272-282.
Goodall, E. V., et al., "Position-selective activation of peripheral nerve fibers with a cuff electrode," IEEE Transactions on Biomedical Engineering, 43(8) (Aug. 1996), pp. 851-856.
Goodall, E. V., "Simulation of activation and propagation delay during tripolar neural stimulation," Proceedings of the 15th Annual International Conference of the IEEE Engineering in Medicine and Biology Society (1993), pp. 1203-1204.
Grill, WM., "Modeling the effects of electric fields on nerve fibers: influence of tissue electrical properties," IEEE Transactions on Biomedical Engineering, 46(8) (1999), pp. 918-928.
Grill, W. M., et al., "Neural and connective tissue response to long-term implantation of multiple contact nerve cuff electrodes," J Biomed Mater Res., 50(2) (May 2000), pp. 215-226.
Grill, W. M., "Neural modeling in neuromuscular and rehabilitation research," Proceedings of the 23rd Annual International Conference of the IEEE Engineering in Medicine and Biology Society, vol. 4 (2001 ), pp. 4065-4068.
Grill, W. M., et al., "Non-invasive measurement of the input-output properties of peripheral nerve stimulating electrodes," Journal of Neuroscience Methods, 65(1) (Mar. 1996), pp. 43-50.
Grill, W. M., et al., "Quantification of recruitment properties of multiple contact cuff electrodes," IEEE Transactions on Rehabilitation Engineering, [see also IEEE Trans. on Neural Systems and Rehabilitation], 4(2) (Jun. 1996), pp. 49-62.
Grill, W. M., "Spatially selective activation of peripheral nerve for neuroprosthetic applications," Ph.D. Case Western Reserve University, (1995), pp. 245 pages.
Grill, W. M., "Stability of the input-output properties of chronically implanted multiple contact nerve cuff stimulating electrodes," IEEE Transactions on Rehabilitation Engineering [see also IEEE Trans. on Neural Systems and Rehabilitation] (1998), pp. 364-373.
Grill, W. M., "Stimulus waveforms for selective neural stimulation," IEEE Engineering in Medicine and Biology Magazine, 14(4) (Jul.-Aug. 1995). pp. 375-385.
Grill, W. M., et al., "Temporal stability of nerve cuff electrode recruitment properties," IEEE 17th Annual Conference Engineering in Medicine and Biology Society, vol. 2 (1995), pp. 1089-1090.
Gross, RE., et al., "Advances in neurostimulation for movement disorders," Neurol Res., 22(3) (Apr. 2000), pp. 247-258.
Guridi et al., "The subthalamic nucleus, hemiballismus and Parkinson's disease: reappraisal of a neurological dogma," Brain, vol. 124, 2001, pp. 5-19.
Haberler, C, et al., "No tissue damage by chronic deep brain stimulation in Parkinson's disease," Ann Neurol., 48(3) (Sep. 2000), pp. 372-376.
Hamel, W, et al., "Deep brain stimuation of the subthalamic nucleus in Parkinson's disease: evaluation of active electrode contacts," J Neurol Neurosurg Psychiatry, 74(8) (Aug. 2003), pp. 1036-1046.
Hanekom, "Modelling encapsulation tissue around cochlear implant electrodes," Med. Biol. Eng. Comput. vol. 43 (2005), pp. 47-55.
Haueisen, J , et al., "The influence of brain tissue anisotropy on human EEG and MEG," Neuroimage, 15(1) (Jan. 2002), pp. 159-166.

D'Haese et al. Medical Image Computing and Computer-Assisted Intervention—MICCAI 2005 Lecture Notes in Computer Science, 2005, vol. 3750, 2005, 427-434.
Rohde et al. IEEE Transactions on Medical Imaging, vol. 22 No. 11, 2003 p. 1470-1479.
Dawant et al., Biomedical Image Registration. Lecture Notes in Computer Science, 2003, vol. 2717, 2003, 142-150.
Miocinovic et al., "Stereotactiv Neurosurgical Planning, Recording, and Visualization for Deep Brain Stimulation in Non-Human Primates", Journal of Neuroscience Methods, 162:32-41, Apr. 5, 2007, XP022021469.
Gemmar et al., "Advanced Methods for Target Navigation Using Microelectrode Recordings in Stereotactic Neurosurgery for Deep Brain Stimulation", 21st IEEE International Symposium on Computer-Based Medical Systems, Jun. 17, 2008, pp. 99-104, XP031284774.
Acar et al., "Safety Anterior Commissure-Posterior Commissure-Based Target Calculation of the Subthalamic Nucleus in Functional Stereotactic Procedures", Stereotactic Funct. Neurosura., 85:287-291, Aug. 2007.
Andrade-Souza, "Comparison of Three Methods of Targeting the Subthalamic Nucleus for Chronic Stimulation in Parkinson's Disease", Neurosurgery, 56:360-368, Apr. 2005.
Anheim et al., "Improvement in Parkinson Disease by Subthalamic Nucleus Stimulation Based on Electrode Placement", Arch Neural., 65:612-616, May 2008.
Butson et al., "Tissue and Electrode Capacitance Reduce Neural Activation Volumes During Deep Brain Stimulation", Clinical Neurophysiology, 116:2490-2500, Oct. 2005.
Butson et al., "Sources and Effects of Electrode Impedance During Deep Brain Stimulation", Clinical Neurophysiology, 117:44 7-454, Dec. 2005.
D'Haese et al., "Computer-Aided Placement of Deep Brain Stimulators: From Planning to Intraoperative Guidance", IEEE Transaction on Medical Imaging, 24:1469-1478, Nov. 2005.
Gross et al., "Electrophysiological Mapping for the Implantation of Deep Brain Stimulators for Parkinson's Disease and Tremor", Movement Disorders, 21 :S259-S283, Jun. 2006.
Halpern et al., "Brain Shift During Deep Brain Stimulation Surgery for Parkinson's Disease", Stereotact Funct. Neurosurg., 86:37-43, published online Sep. 2007.
Herzog et al., "Most Effective Stimulation Site in Subthalamic Deep Brain Stimulation for Parkinson's Disease", Movement Disorders, 19:1050-1099, published on line Mar. 2004.
Jeon et al., A Feasibility Study of Optical Coherence Tomography for Guiding Deep Brain Probes, Journal of Neuroscience Methods, 154:96-101, Jun. 2006.
Khan et al., "Assessment of Brain Shift Related to Deep Brain Stimulation Surgery", Sterreotact Funct. Neurosurg., 86:44-53, published online Sep. 2007.
Koop et al., "Improvement in a Quantitative Measure of Bradykinesia After Microelectrode Recording in Patients with Parkinson's Disease During Deep Brain Stimulation Surgery", Movement Disorders, 21 :673-678, published on line Jan. 2006.
Lemaire et al., "Brain Mapping in Stereotactic Surgery. A Brief Overview from the Probabilistic Targeting to the Patient-Based Anatomic Mapping", NeuroImage, 37:S109-S115, available online Jun. 2007.
Machado et al., "Deep Brain Stimulation for Parkinson's Disease: Surgical Technique and Perioperative Management", Movement Disorders, 21 :S247-S258. Jun. 2006.
Maks et al., "Deep Brain Stimulation Activation Volumes and Their Association with Neurophysiological Mapping and Therapeutic Outcomes", Downloaded from jnnp.bmj.com, pp. 1-21, published online Apr. 2008.
Moran et al., "Real-Time Refinment of Subthalamic Nucleous Targeting Using Bayesian Decision-Making on the Root Mean Square Measure", Movement Disorders, 21: 1425-1431, published online Jun. 2006.
Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.

(56) References Cited

OTHER PUBLICATIONS

Winkler et al., The First Evaluation of Brain Shift During Functional Neurosurgery by Deformation Field Analysis, J. Neural. Neurosurg. Psychiatry, 76:1161-1163, Aug. 2005.
Yelnik et al., "A Three-Dimensional, Histological and Deformable Atlas of the Human Basal J Ganglia. I. Atlas Construction Based on Immunohistochemical and MRI Data", NeuroImage, 34:618,-638,Jan. 2007.
Ward, H. E., et al., "Update on deep brain stimulation for neuropsychiatric disorders," Neurobiol Dis 38 (3) (2010), pp. 346-353.
Alberts et al. "Bilateral subthalamic stimulation impairs cognitive-motor performance in Parkinson's disease patients." Brain (2008), 131, 3348-3360, Abstract.
Mayberg, H. S., et al., "Deep brain stimulation for treatment-resistant depression," Neuron, 45(5) (Mar. 3, 2005), pp. 651-660.
An, et al., "Prefronlal cortical projections to longitudinal columns in the midbrain periaqueductal gray in macaque monkeys," J Comp Neural 401 (4) (1998), pp. 455-479.
Mayberg, H. S., et al., "Limbic-cortical dysregulation a proposed model of depression," J Neuropsychiatry Clin Neurosci. 9 (3) (1997), pp. 471-481.
Carmichael, S. T., et al., "Connectional networks within the orbital and medial prefronlal cortex of macaque monkeys," J Comp Neural 371 (2) (1996), pp. 179-207.
Croxson, et al., "Quantitative investigation of connections of the prefronlal cortex in the human and macaque using probabilistic diffusion tractography," J Neurosci 25 (39) (2005), pp. 8854-8866.
Frankemolle, et al., "Reversing cognitive-motor impairments in Parkinson's disease patients using a computational modelling approach to deep brain stimulation programming," Brain 133 (2010), pp. 746-761.
Freedman, et al., "Subcortical projections of area 25 (subgenual cortex) of the macaque monkey," J Comp Neurol 421 (2) (2000), pp. 172-188.
Giacobbe, et al., "Treatment resistant depression as a failure of brain homeostatic mechanisms: implications for deep brain stimulation," Exp Neural 219 (1) (2009), pp. 44-52.
Goodman, et al. "Deep brain stimulation for intractable obsessive compulsive disorder: pilot study using a blinded, staggered-onset design," Biol Psychiatry 67 (6) (2010), pp. 535-542.
Greenberg, et al., "Deep brain stimulation of the ventral internal capsule/ventral striatum for obsessive-compulsive disorder: world-wide experience," Mol Psychiatry 15 (1) (2010), pp. 64-79.
Greenberg, et al., "Three-year outcomes in deep brain stimulation for highly resistant obsessive-compulsive disorder," Neuropsychopharmacology 31 (11) (2006), pp. 2384-2393.
Gutman, et al., "A tractography analysis of two deep brain stimulation white matter targets for depression," Biol Psychiatry 65 (4) (2009), pp. 276-282.
Haber, et al., "Reward-related cortical inputs define a large striatal region in primates that interface with associative cortical connections, providing a substrate for incentive-based learning," J Neurosci 26 (32) (2006), pp. 8368-8376.
Haber, et al., "Cognitive and limbic circuits that are affected by deep brain stimuation," Front Biosci 14 (2009), pp. 1823-1834.
European Patent Office, International Searching Authority, International Search Report and the Written Opinion of the ISA in International Application No. PCT/US2011/040329, dated Dec. 29, 2011, 14 pages.
European Patent Office, International Searching Authority, International Search Report and the Written Opinion of the ISA in International Application No. PCT/US2012/069667, dated Feb. 27, 2013, 15 pages.
European Patent Office, International Searching Authority, Partial International Search Report of the ISA in International Application No. PCT/US2013/056981, dated May 6, 2014, 4 pages.
European Patent Office, International Search Report and the Written Opinion of the ISA in International Application No. PCT/US2013/056975, dated Feb. 20, 2014, 11 pages.
European Patent Office, International Search Report and the Written Opinion of the ISA in International Application No. PCT/US2013/056984, dated Dec. 10, 2013, 11 pages.
European Patent Office, International Search Report and the Written Opinion/ISA in International Patent Application No. PCT/US2013/056112, dated May 15, 2014, 14 pages.
European Patent Office, International Search Report in International Application No. PCT/US2012/053344, dated Nov. 26, 2012, 8 pages.
European Patent Office, International Search Report in International Application No. PCT/US2012/050181, dated Jan. 3, 2013, 7 pages.
Euopean Patent Office, International Search Report and the Written Opinion in International Application No. PCT/US2012/050170, dated Oct. 5, 2012, 15 pages.
European Patent Office, International Search Report in International Application No. PCT/US09/03017, dated Aug. 3, 2009, 7 pages.
European Patent Office, International Search report and Written Opinion in PCT application No. PCT/US12/050174, dated Mar. 6, 2013, 20 pages.
European Patent Office, International Search Report and Written Opinion in International Application No. PCT/US2012/050187, dated Feb. 27, 2013, 9 pages.
European Patent Office, International Search Report and Written Opinion in International Application No. PCT/US2012/030700, dated Feb. 27, 2013, 9 pages.
European Patent Office, International Search Report in International Application No. PCT/US09/03041, dated Aug. 20, 2009, 7 pages.
European Patent Office, International Search Report and the Written Opinion of the International Searching Authority in International Application No. PCT/US2012/050175, dated Oct. 26, 2012, 15 pages.
European Patent Office, International Search Report in International Application No. PCT/US09/03038, dated Oct. 8, 2009, 9 pages.
European Patent Office, International Search Report in International Application No. PCT/US09/03040, dated Aug. 13, 2009, 7 pages.
European Patent Office, International Search Report in International Application No. PCT/US09/03049, dated Jan. 26, 2010, 8 pages.
European Patent Office, partial International Search Report in International Application No. PCT/US2012/030701, dated Feb. 15, 2013, 7 pages.
European Patent Office, partial International Search Report in International Application No. PCT/US2012/030705, dated Mar. 6, 2013, 7 pages.
Butson et al., "Current Steering to Control the Volume of Tissue Activated During Deep Brain Stimulation," Brain Stimulation 1, 2008, pp. 7-15.
Butson et al., "Patient Specific Analysis of the volume of tissue activated during deep brain stimulation," NeuroImage, Academic Press, vol. 34, No. 2, Dec. 2, 2006, pp. 661-670.
Butson et al., "Role of Electrode Design on the Volume of Tissue Activated During Deep Brain Stimulation," Journal of Neural Engineering, Mar. 1, 2006, vol. 3, No. 1, pp. 1-8.
Butson et al., "StimExplorer: Deep Brain Stimulation Parameter Selection Software System," Acta Neurochirugica, Jan. 1, 2007, vol. 97, No. 2, pp. 569-574.
Carnevale, N.T., et al., "The Neuron Book," Cambridge, UK: Cambridge University Press (2006), 480 pages.
Chaturvedi, "Development of Accurate Computational Models for Patient-Specific Deep Brain Stimulation," Electronic Thesis or Dissertation, Jan. 2012, 162 pages.
Chaturvedi A et al., "Patient-specific models of deep brain stimulation: Influence of field model complexity on neural activation predictions," Brain Stimulation, Elsevier, Amsterdam, NL, vol. 3, No. 2, Apr. 2010, pp. 65-77.
Commowick, Olivier, et al., "Using Frankenstein's Creature Paradigm to Build a Patient Specific Atlas," Sep. 20, 2009, Medical Image Computing and Computer-Assisted Intervention, pp. 993-1000.
Cover, T.M., et al., "Elements of information theory," (1991) John Wiley & Sons, New York, NY, pp. 1-542.
Dice, Lee R., "Measures of the Amount of Ecologic Association Between Species," Ecology 26(3) (1945), pp. 297-302, doi:10.2307/1932409, http://jstor.org/stable/1932409.

(56) References Cited

OTHER PUBLICATIONS

Ericsson, A., et al., "Construction of a patient-specific atlas of the brain: Application to normal aging," Biomedical Imaging: From Nano to Macro, ISBI 2008, 5th IEEE International Symposium, May 14, 2008, pp. 480-483.
Hubert, Lawrence, et al., "Comparing partitions," Journal of Classification 2(1) (1985), pp. 193-218, doi:10.1007/BF01908075.
Izad, Olivier, "Computationally Efficient Method in Predicating Axonal Excitation," Dissertation for Masters Degree, Department of Biomedical Engineering, Case Western Reserve University, May 2009, 144 pages.
Jaccard, Paul, "Étude comparative de la distribution florale dans une portion odes Aples et des Jura," Bulletin de la Société Vaudoise des Sciences Naturelles (1901), vol. 37, pp. 547-579.
Klein, A., et al., "Evaluation of 14 nonlinear deformation algorithms applied to human brain MRI registration," NeuroImage, Academic Press, Orlando, FL, vol. 46, No. 3, Jul. 2009, pp. 786-802.
Liliane Ramus et al, "Assessing selection methods in the context of multi-atlas based segmentation," Biomedical Imaging: From Nano to Macro, 2010 IEEE International Symposium, Apr. 14, 2010, pp. 1321-1324.
Lotjonen, J.M.P., et al, "Fast and robust multi-atlas segmentation of brain magnetic resonance images," NeuroImage, Academic Press, vol. 49, No. 3, Feb. 1, 2010, pp. 2352-2365.
McIntyre, C.C., et al., "Modeling the excitability of mammalian nerve fibers: influence of afterpotentials on the recovery cycle," J Neurophysiol, 87(2) (Feb. 2002), pp. 995-1006.
Meila, Marina, "Comparing Clusterings by the Variation of Information," Learning Theory and Kernel Machines (2003), pp. 173-187.
Miocinovic et al., "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.
Peterson et al., "Predicting myelinated axon activation using spatial characteristics of the extracellular field," Journal of Neural Engineering, 8 (2011), 12 pages.
Rand, W.M., "Objective criteria for the evaluation of clustering methods," Journal of the American Statistical Association (American Statistical Association) 66 (336) (1971), pp. 846-850, doi:10.2307/2284239, http://jstor.org/stable/2284239.
Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.
Schmidt et al., "Sketching and Composing Widgets for 3D Manipulation," Eurographics, Apr. 2008, vol. 27, No. 2, pp. 301-310.
Shen, Kaikai, et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.
Siegel, Ralph M. et al., "Spatiotemporal dynamics of the functional architecture for gain fields in inferior parietal lobule of behaving monkey," Cerebral Cortex, New York, NY, vol. 17, No. 2, Feb. 2007, pp. 378-390.
Volkmann, J., et al., "Introduction to the programming of deep brain stimulators," Mov. Disord., vol. 17 (Suppl 3) (2002), pp. 181-187.
Warman et al., "Modeling the Effects of Electric Fields on nerve Fibers: Determination of Excitation Thresholds," IEEE Transactions on Biomedical Engineering, vol. 39, No. 12 (Dec. 1992), pp. 1244-1254.
Wesselink et al., "Analysis of Current Density and Related Parameters in Spinal Cord Stimulation," IEEE Transactions on Rehabilitation Engineering, vol. 6, No. 2, Jun. 1998, pp. 200-207.

\* cited by examiner

PROGRAMMING INTERFACE FOR SPINAL CORD NEUROMODULATION

CROSS-REFERENCE TO RELATED APPLICATIONS

The present application is a divisional application of U.S. Patent Application Ser. No. 13/160,104, filed Jun. 14, 2011, which claims the benefit of priority to U.S. Provisional Application Ser. Nos. 61/354,576, filed Jun. 14 2010 and 61/37,6439, filed Aug. 24, 2010, the entirety of each of which is hereby incorporated by reference herein.

TECHNICAL FIELD

The present invention relates generally to programming for electrical stimulation of the spinal cord.

BACKGROUND

Spinal cord stimulation can be used to treat chronic pain by providing electrical stimulation pulses from an electrode array implanted in close proximity to a patient's spinal cord. It is desirable to tailor the electrical stimulation parameters (such as electrode contact selection, polarity selection, pulse amplitude, pulse width, and pulse rate) for treatment of a particular patient. However, the process of selecting stimulation parameters can be time consuming and may require a great deal of trial-and-error before a suitable therapeutic program is found. Often, these parameters are selected based on intuition or some other idiosyncratic methodology. Because the programming of spinal cord stimulation can be such a cumbersome process, there is a need for assistance in the planning or performing of electrical stimulation of a patient's spinal cord.

SUMMARY

The present invention provides a tool for assisting in the planning or performing of electrical neuromodulation of a patient's spinal cord. The tool may be embodied as computer software or a computer system. In certain embodiments, the present invention provides a method for assisting the planning or performing of spinal cord neuromodulation in a patient, comprising: (a) having a functional image of the patient's spinal anatomy, wherein the functional image of the spinal anatomy includes an electrode and information defining functional regions of the spinal anatomy according to one or more neurologic functions; (b) determining the position of the electrode relative to the functional regions; (c) selecting a target functional region of the spinal anatomy; (d) having an electric field model of an electrode positioned adjacent the patient's spinal cord; and (e) determining one or more electrode neuromodulation settings that produces a volume of activation that at least partially encompasses the targeted functional region of the spinal anatomy.

In certain embodiments, the present invention provides a method for assisting the planning or performing of spinal cord neuromodulation in a patient, comprising: (a) receiving a first radiologic image of an electrode inside a patient, wherein the electrode is in a first position; (b) receiving a second radiologic image of the electrode after a change in the position of the electrode, wherein the electrode is in a second position; (c) determining the position of the electrode in the second position relative to the electrode in the first position; (d) calculating a first volume of activation generated by the electrode in the first position; and (e) determining an electrode neuromodulation setting for the electrode in the second position that produces a second volume of activation that at least partially encompasses the first volume of activation.

In certain embodiments, the present invention provides a method for assisting the planning or performing of spinal cord neuromodulation in a patient, comprising: (a) receiving a radiologic image of the patient showing one or more electrodes inside the patient; (b) locating the one or more electrodes in the radiologic image, wherein the one or more electrodes collectively have multiple electrode contacts; and (c) determining a functional midline for the one or more electrodes.

In certain embodiments, the present invention provides a method for assisting the planning or performing of spinal cord neuromodulation in a patient, comprising: (a) having an electric field model of an electrode positioned adjacent a spinal cord, wherein the model includes a representation of the depth of the cerebrospinal fluid between the electrode and the spinal cord; and (b) using the electric field model to calculate a volume of activation created by the electrode under a set of electrode neuromodulation conditions.

In certain embodiments, the present invention provides a method for assisting the planning or performing of spinal cord neuromodulation in a patient, comprising: (a) receiving a first radiologic image showing an electrode and a spinal anatomy of the patient; (b) receiving a second radiologic image showing the electrode and the spinal anatomy of the patient, wherein the second radiologic image provides a different view than the first radiologic image; and (c) using the first radiologic image and the second radiologic image to determine the three-dimensional position of the electrode in relation to the spinal anatomy.

BRIEF DESCRIPTION OF THE DRAWINGS

FIG. 1A shows an anterior-posterior view and FIG. 1B shows a lateral view of the spine.

FIG. 12A shows the electrode prior to migration and FIG. 12B shows the electrode after migration.

DETAILED DESCRIPTION

Figure 1A:
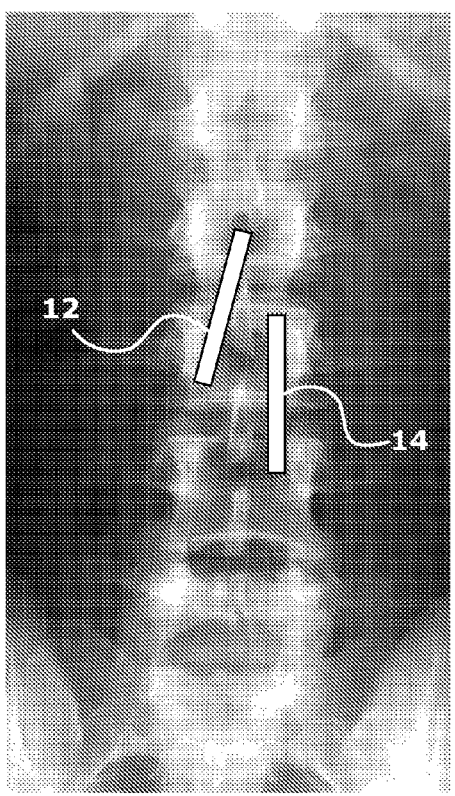
FIGS. 1A and 1B show x-ray images of a patient's spine with two electrodes that are implanted in the spine.

The present invention provides a tool for assisting in the planning or performing of electrical neuromodulation of a patient's spinal cord (sometimes referred to in the art as spinal cord stimulation). In certain embodiments, the tool provides a simulation of how much volume of neural tissue is affected by the electrical neuromodulation. As used herein, the term "volume of activation" means a volume of neural tissue in which the neurons are activated by the electric field being applied to the neural tissue during electrical neuromodulation. Neural activation may have a stimulatory effect or an inhibitory effect on the neural tissue, or a combination of both. Although the volume refers to a three-dimensional space, the calculation, analysis, and/or displaying of the volume as described herein does not necessarily have to be performed in three dimensions. Such actions may be performed in two dimensions instead. For example, the volume of activation may be calculated in a two-dimensional plane and shown as a two-dimensional image.

The present invention may use any suitable method for calculating a volume of activation for neural tissue. For example, methods for calculating a volume of activation suitable for use in the present invention include those described in U.S. Pat. No. 7,346,382 (McIntyre et al.), U.S. Patent Application Publication No. 2007/0288064 (Butson et al.), and U.S. Patent Application Publication No. 2009/0287271 (Blum et al.), which are incorporated in their entirety by reference herein. In certain embodiments, to calculate a volume of activation, the tool uses a mathematical model of the electric field generated by one or more electrodes positioned adjacent the spinal cord of a patient. The mathematical model may be any suitable type of model that can be used to model an electric field created by an electrode, such as finite element models of the electrode(s) and the tissue medium.

The electric field generated by an electrode is dependent upon various conditions of the electrode itself, including the electrode position, electrode orientation, electrode configuration, electrode contact polarity, electrode contact selection, electrode contact capacitance, electrode contact impedance, and waveform parameters (e.g., shape, pulse width, frequency, voltage, etc.). As used herein, "electrode neuromodulation conditions" refers to one or more of these factors. A set of electrode neuromodulation conditions may include one or more of these factors. For a given set of electrode neuromodulation conditions, the tool can calculate a volume of activation produced by the electrode. As used herein, the term "electrode neuromodulation settings" refers to a subset of electrode neuromodulation conditions that relate more specifically to the electrode contacts and can be adjusted during the operation of the electrode to vary the electric field. Examples of electrode neuromodulation settings include electrode contact selection and waveform parameters (e.g., shape, pulse width, frequency, voltage, etc.).

As used herein, the term "electrode" refers to the lead body along with the electrode contacts on the lead body. When referring to position, it is convenient to refer to the electrode as a whole, rather than referring to the position of the electrode contacts or lead body individually because the electrodes contacts are fixed on the lead body. Therefore, if the position of the electrode contacts relative to the lead body is known, then the position of the electrode contacts can be determined from the position of the lead body, and vice versa. Because of this fixed relationship, any reference to the position of the electrode is intended to include the position of the lead body and the electrode contacts as well. Also, when referring to the "position" of the electrode, this is intended to include the orientation of the electrode as well.

The electric field model can be solved for the spatial and temporal voltage distribution that represents the electric field that is created in the tissue medium by the electrode according to a particular set of electrode neuromodulation conditions. In certain embodiments, the electric field model is coupled to a neuron model to determine whether the electric potential at a given point in space is sufficient to activate neurons in the tissue medium. The boundaries of neuronal activation predicted by the neuron model determines the volume of activation. Examples of such methods that can be used in the present invention include those described in U.S. Pat. No. 7,346,382 (McIntyre et al.), U.S. Patent Application Publication No. 2007/0288064 (Butson et al.), and U.S. Patent Application Publication No. 2009/0287271 (Blum et al.), which are incorporated by reference herein. Where radiologic imaging of the spinal anatomy is available, the model axons of the neuron model can be aligned to the orientation of the spinal cord or spinal column.

Another way in which the volume of activation can be determined is by calculating the second order spatial derivative of the electric potential that is distributed around the electrode. The second spatial derivative is then compared against an activation threshold. The activation threshold is the threshold value at which a neuron is activated at that particular point in space for the tissue medium. If the second spatial derivative of the electric potential exceeds the activation threshold, then the neuron at that point in space is considered to be activated. The second order spatial derivative can be calculated by numerical or approximation techniques. For example, the second difference of the electrical potential can be used to approximate the second order derivative, as described in U.S. Pat. No. 7,346,382 (McIntyre et al.), U.S. Patent Application Publication No. 2007/0288064 (Butson et al.), and U.S. Patent Application Publication No. 2009/0287271 (Blum et al.), which are incorporated by reference herein.

These activation thresholds are determined from the application of the calculated electric field to the neuron model, as described above. However, the manner in which the activation thresholds are provided can vary according to different embodiments of the present invention. In some embodiments, these activation thresholds can be calculated during the operation of the tool. However, it is also possible to have these activation thresholds calculated prior to the operation of the tool. In this case, the activation thresholds are predefined for use during the operation of the tool. For example, based on the pre-calculations, equations may be formulated that give the activation thresholds as a function of distance from the electrode and one or more electrode neuromodulation conditions (such as pulse width and voltage). Thus, during operation of the tool, the tool may use one or more of these equations to calculate the activation thresholds by inputting the relevant values into the equation and solving the equations to obtain a spatial map of the activation thresholds. Thus, based on a given set of neuromodulation conditions, the spatial contour of the activation thresholds can be established and used to determine the volume of activation as the isosurface where the second spatial derivative is suprathreshold. In addition to these methods, other methods for determining a volume of activation by an electrode can be used in the present invention, such as those methods described in U.S. Patent Application Publication No. 2007/0288064 (Butson et al.) and U.S. Patent Application Publication No. 2009/0287271 (Blum et al.), which are incorporated by reference herein.

Electrode Registration

In certain embodiments, the tool may use a radiologic image in performing the functions that are described herein. The radiologic image may show the electrodes and/or various portions of the patient's spinal anatomy. As used herein, "spinal anatomy" means the anatomy relating to the spinal column, which includes the spinal cord, the vertebral bodies, nerves, and/or other soft or bony tissue of the spinal column. The radiologic image may be any type of body imaging used in medicine, such as x-rays (including conventional film and fluoroscopic x-rays), magnetic resonance imaging (MRI), computed tomography (CT), positron emission tomography (PET), etc. For example, the radiologic image may be an anterior-posterior view or a lateral view x-ray of the patient's spine. The radiologic image may not necessarily show all portions of the spinal anatomy. The portion of the patient's spinal anatomy that is visible on the radiologic image will depend upon the type of imaging modality used. For example, in x-ray images, only the bony structures may be visible in the image (but not the spinal cord itself). In MR images, the spinal cord itself may be visible, in addition to the bony and other soft tissue elements.

In the tool, the radiologic images are embodied as data structures (e.g., digital images). In some cases, the radiologic image may be used to register the location of the electrode. For example, the tool may register the electrode relative to a landmark of the spinal anatomy that is visible on the radiologic image. For example, in the case of x-ray images, the location of the electrode can be registered relative to the vertebral bodies that are visible on the image. As will be explained below, the location of the electrode relative to the spinal cord itself can be estimated based on the association between the vertebral level and the spinal cord level.

As explained above, when referring to position, it is convenient to refer to the electrode as a whole, rather than referring to the position of the electrode contacts or lead body individually because the electrode contacts are fixed on the lead body. As a result, if the position of the lead body is registered by the tool, then the electrode contacts on the lead body can also be considered to be registered as well, and vice versa. Whether the tool will locate the lead body or the electrode contacts directly will depend on a variety of factors, such as its visibility in the radiologic image. Since the lead body is larger, in some cases, it may be more practical to locate the lead body and then locate the position of the electrode contacts based on the lead body position. In other cases, since the electrode contacts may be more radiopaque and more readily identifiable on CT or x-ray, it may be more practical to locate the electrode contacts in the image.

The electrode can be located automatically or manually in the radiologic image. Example methods of locating and registering an electrode that can be used in the present invention are described in U.S. Patent Application Publication No. 2009/0287271 (Blum et al.), which is incorporated by reference herein.

Where there are multiple electrodes (two or more) present in the radiologic image, the tool may determine the position of the electrodes in relation to each other and/or the spinal anatomy. In some cases, three-dimensional positional information can be reconstructed from multiple (two or more) different two-dimensional views of the electrode and the angle between the different views. This three-dimensional reconstruction can be performed using any suitable technique known in the art.

Figure 1B:
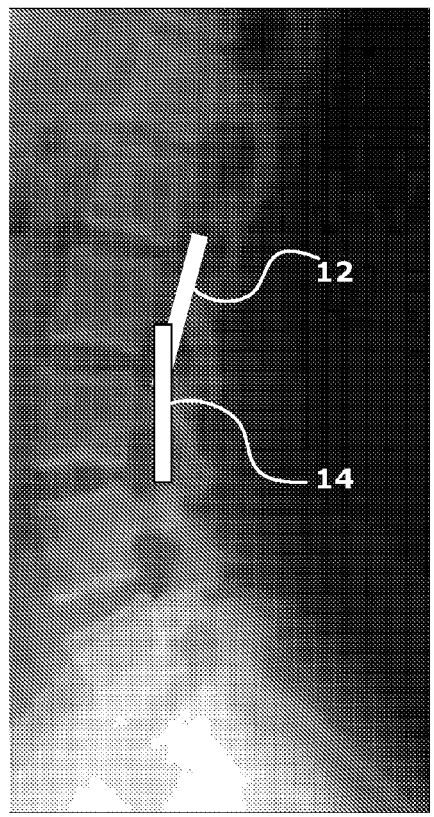

For example, FIGS. 1A and 1B show x-ray images that can be used to locate and reconstruct the three-dimensional position of two electrodes 12 and 14 that have been implanted in a patient's spine. FIG. 1A shows an anterior-posterior view of the spine with electrodes 12 and 14 visible in the x-ray image. The tool registers the position of electrodes 12 and 14 relative to each other and/or the spinal anatomy.

FIG. 1B shows a lateral view of the spine with electrodes 12 and 14 visible in the x-ray image. The tool registers the position of electrodes 12 and 14 relative to each other, and optionally, with the spinal anatomy. Having these two different perspective views (at a 90° angle) of electrodes 12 and 14, the tool can now reconstruct the three-dimensional position of electrodes 12 and 14 relative to each other, and optionally, the spinal anatomy. Thus, the tool can display a reconstructed three-dimensional view of electrodes 12 and 14 with respect to each other and/or the spinal anatomy.

Thus, in certain embodiments, the tool may receive a first radiologic image (e.g., an anterior-posterior view x-ray) showing an electrode and the spinal anatomy of the patient, and receive a second radiologic image (e.g., a lateral view x-ray) showing the electrode and the spinal anatomy of the patient. The second radiologic image provides a different view than the first radiologic image so that they can be used to determine the three-dimensional position of the electrode in relation to the spinal anatomy. In some cases, the first and second radiologic images are used to determine the three-dimensional position of the multiple electrodes in relation to each other. Once the position of the electrodes is determined, a three-dimensional image of the electrodes and the spinal anatomy may be displayed to the user. The three-dimensional image may be rotated, panned, and zoomed to allow the user to precisely explore the actual device positioning in space.

Functional Images

In certain embodiments, in addition to anatomical structures, the radiologic image of the spinal anatomy may include information associating parts of the image to one or more neurologic functions (i.e., a functional image). The functional image may also include other symbolic information, such as structure names, object features, target volumes generated from previous patient data, anatomic landmarks, or boundaries. The neurologic functions in the functional image may be either motor or sensory functions. In some cases, the functional image may define different levels of the spinal cord in the image. For example, the functional image may include information that associates different parts of the image with the dermatomes that are innervated by the different spinal cord levels, as will be further explained below.

Functional information can be incorporated into the image data using any suitable technique known in the art. In some cases, the functional information is incorporated by registering a patient-specific radiologic image to a standard atlas of the same anatomy. A standard atlas is an atlas of the spinal anatomy that is intended to represent the typical or normal anatomy that is present in human beings. As such, the standard atlas can be derived from a composite of the anatomy of multiple individuals to be representative of "normal" or "typical" human anatomy. The tool may have multiple standard atlases (e.g., variants of normal anatomy) and allow the user to select one that is a closest match to the patient being treated.

Registration of the patient-specific image to the standard atlas may be performed using any suitable technique known in the art, including the methods described in U.S. Patent Application Publication No. 2009/0287271 (Blum et al.). For example, the image registration process may involve a transformation of the patient-specific image to match or fit the standard atlas, a transformation of the standard atlas to match or fit the patient-specific image, or some combination of both. In some cases, the image registration process may use anatomic landmarks that have been established in the image. These anatomic landmarks can be identified manually by a user or automatically by the tool. For example, in an x-ray of the spine, the vertebral bodies may be identified and registered into the image. Once the anatomic landmarks are identified, the patient-specific radiologic image can be scaled or morphed to fit the standard atlas using the transformation process described above.

Figure 2A:
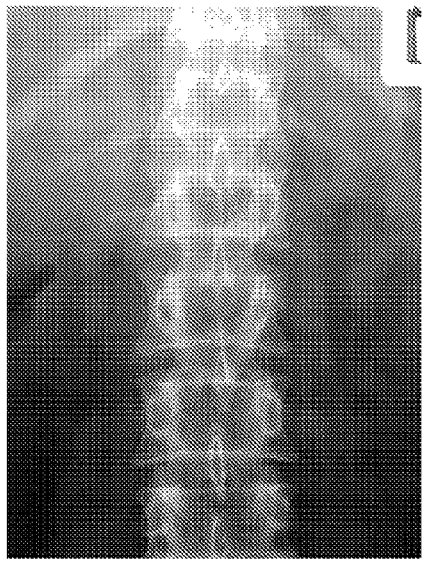
FIG. 2A shows an anterior-posterior view x-ray image of a patient's spine.
Figure 2B:
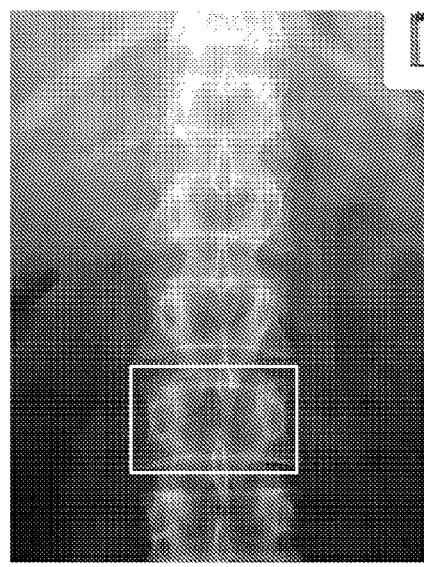
FIG. 2B shows the user identifying a vertebrae.

For example, FIG. 2A shows an x-ray image of a patient's spine, which is imported into the tool. The spinal cord is not visible on the x-ray, but is located within the vertebral spine (i.e., spinal column), which is made up of a column of vertebral bodies (vertebrae). As seen in FIG. 2B, the user identifies the different vertebrae that are visible on the x-ray image by drawing a box around each of the vertebrae. The spinal cord itself is functionally divided into segmental levels defined by the spinal roots that enter and exit the spinal column between each of the vertebral body levels.

Figure 3:
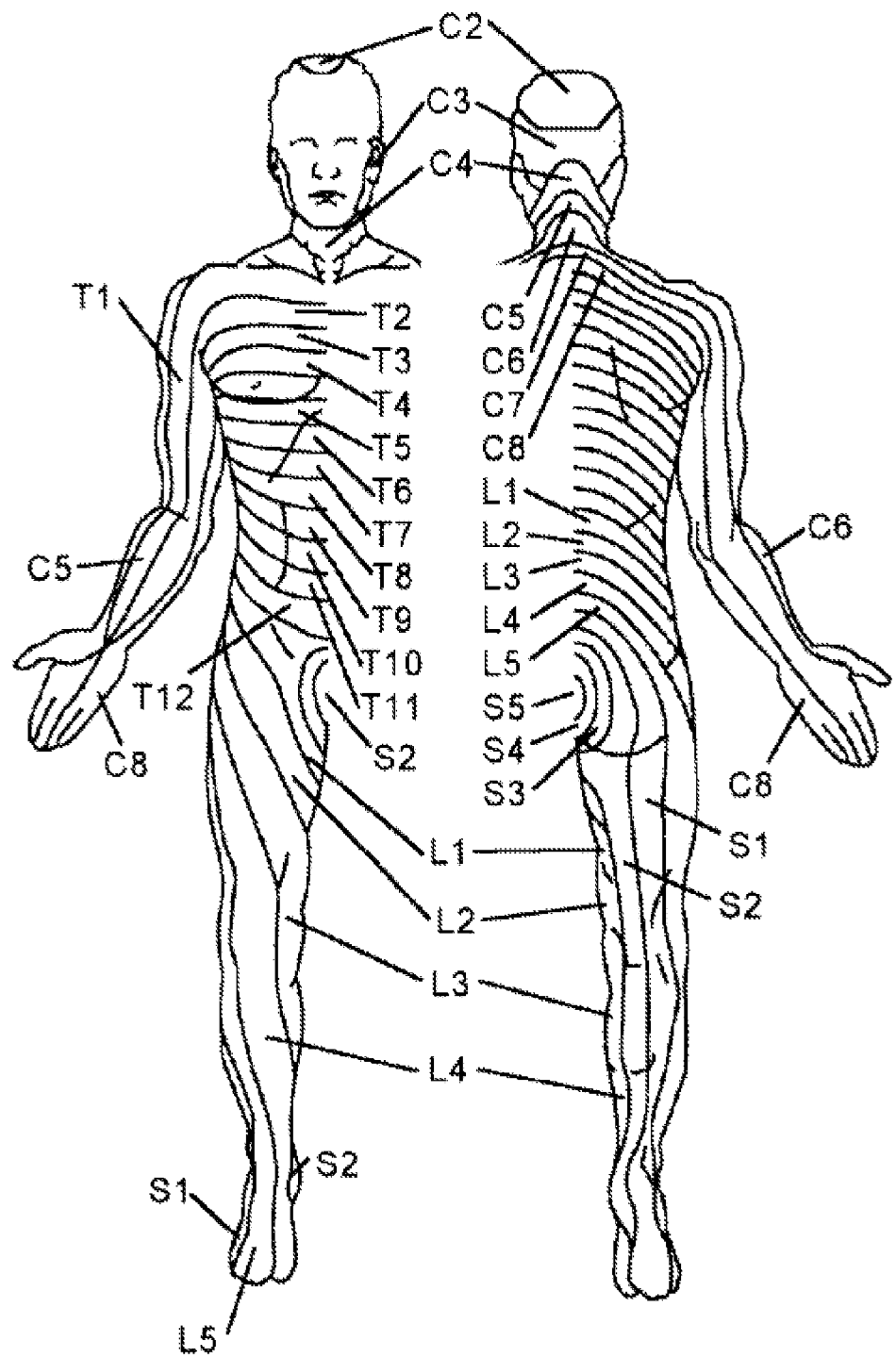
FIG. 3 shows a dermatome map of the human body.

A dermatome is an area of the skin that is predominantly innervated by nerves originating from a single spinal level. FIG. 3 shows a dermatome map of the human body. Thus, the spinal cord can be divided functionally into segments that correspond to different dermatomes. The spinal cord segmental levels do not necessarily correspond to the same level of the vertebral body. Accordingly, the dermatomes innervated by the different spinal cord levels do not necessarily correspond to the vertebral levels. For example, the L5 dermatome level for low back pain may correspond to the T10 vertebral level. However, based on known anatomic and physiologic relationships, the tool of the present invention can make the appropriate correlation between the dermatome levels, the spinal cord levels, and/or the vertebral levels. This association may be useful where the vertebral bodies are being used as a reference for the position of the electrode.

Figure 2C:
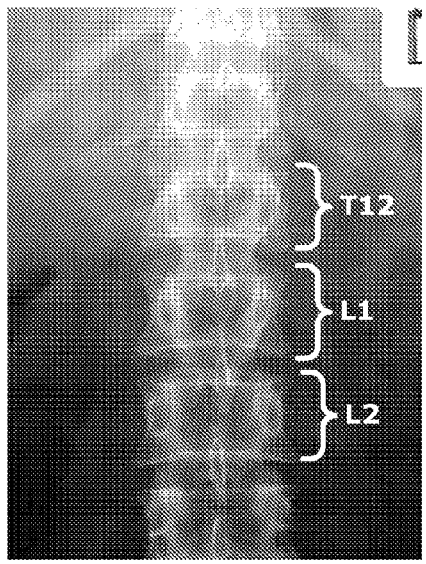
FIG. 2C shows the registration of spinal cord levels into the x-ray image.

As seen in FIG. 2C, the association of these different vertebral levels with their spinal cord levels are registered into the image to create a functional image in which spinal cord levels T12, L1, and L2 are registered as functional regions in the image in association with the vertebral levels that are visible in the image. If electrodes are also present in the image, the electrodes can also be identified (either manually or automatically) and their position registered in relation to the functional regions.

As an alternative to having the user identify each vertebra, the positions of the vertebrae may be identified based on a user identification of a single vertebra in an image. For example, the user may input a vertebral outline, or part of a vertebral outline, along with an identification of the vertebra to which the outline corresponds (e.g., T1). The image is then analyzed to extrapolate the positions of the remaining vertebrae based on their relative positions to the outlined vertebra.

Targeting of Neuromodulation

In certain embodiments, the tool can be used to select a region of the spinal cord as a target for electrical neuromodulation. The selection of the target region can be provided in any suitable manner. For example, the targeted region can be input by the user as a specific anatomic structure (such as a vertebral level), a segment of the spinal cord, a dermatome level, or an area of the body where the patient is experiencing pain or discomfort. In the example where the user indicates one or more dermatome levels as a targeted region, the tool may determine the spinal cord level(s) and/or vertebral level(s) that correspond to those dermatomes. In the example where the user indicates where the patient is experiencing pain or discomfort, the tool may determine the one or more dermatomes associated with that part of the body, and then select one or more spinal cord levels and/or vertebral levels that correspond to that dermatome.

Having selected the targeted region, the tool can then find a set of electrode neuromodulation conditions that would direct the electrical neuromodulation to that targeted region by comparing the predicted volumes of activation against the targeted region. For example, the tool may use a scoring technique that measures the effectiveness of the neuromodulation based on how much of the predicted volume of activation encompasses the targeted region, how much of the targeted region is within the predicted volume of activation, how much of the predicted volume of activation is outside the targeted region, how much of the targeted region is outside the predicted volume of activation, how much of the predicted volume of activation encompasses neural tissue that would cause side effects, or a combination thereof. The tool may calculate multiple predicted volumes of activation under different neuromodulation conditions in order to find a suitable set of electrode neuromodulation conditions. When a combination of scoring factors is used, the different factors may be weighted differently according to their relative importance in determining the therapeutic effectiveness of the neuromodulation. In some cases, an improved or optimal set of neuromodulation conditions can be determined by using an optimization algorithm to find a set of electrode neuromodulation conditions that produces a volume of activation having the best score (e.g., highest or lowest score).

Figure 4:
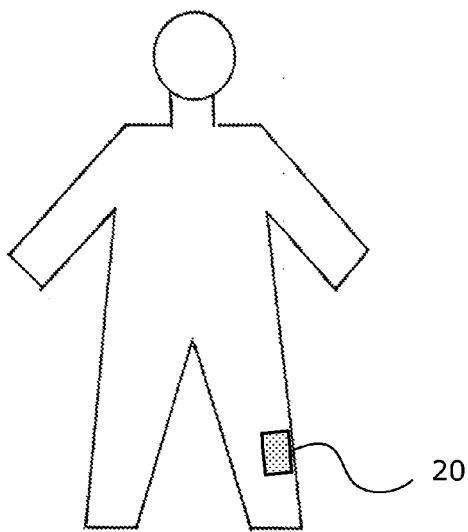
FIG. 4 shows a human figure that may be displayed by the tool with the area of pain indicated in the human figure.
Figure 5:
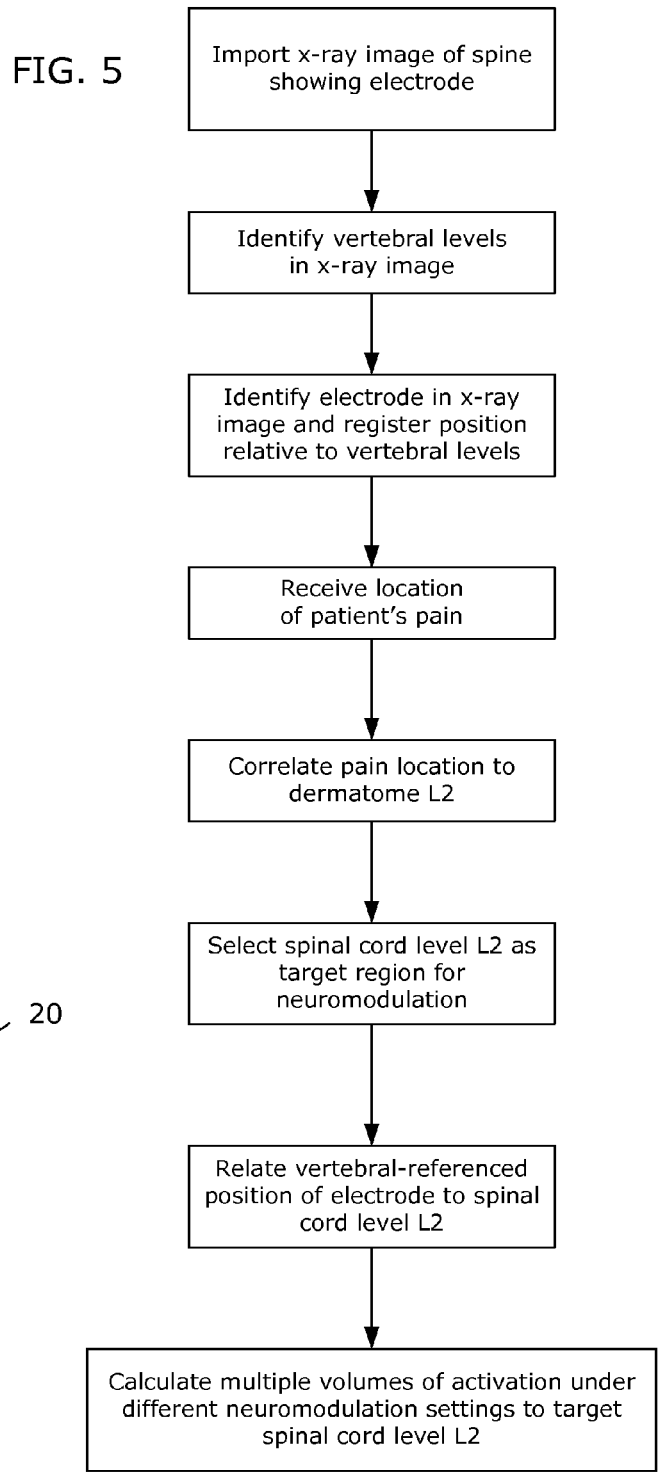
FIG. 5 shows a flowchart illustrating an example of how spinal cord neuromodulation can be targeted based on the location of the pain on a patient's body.
Figure 6:
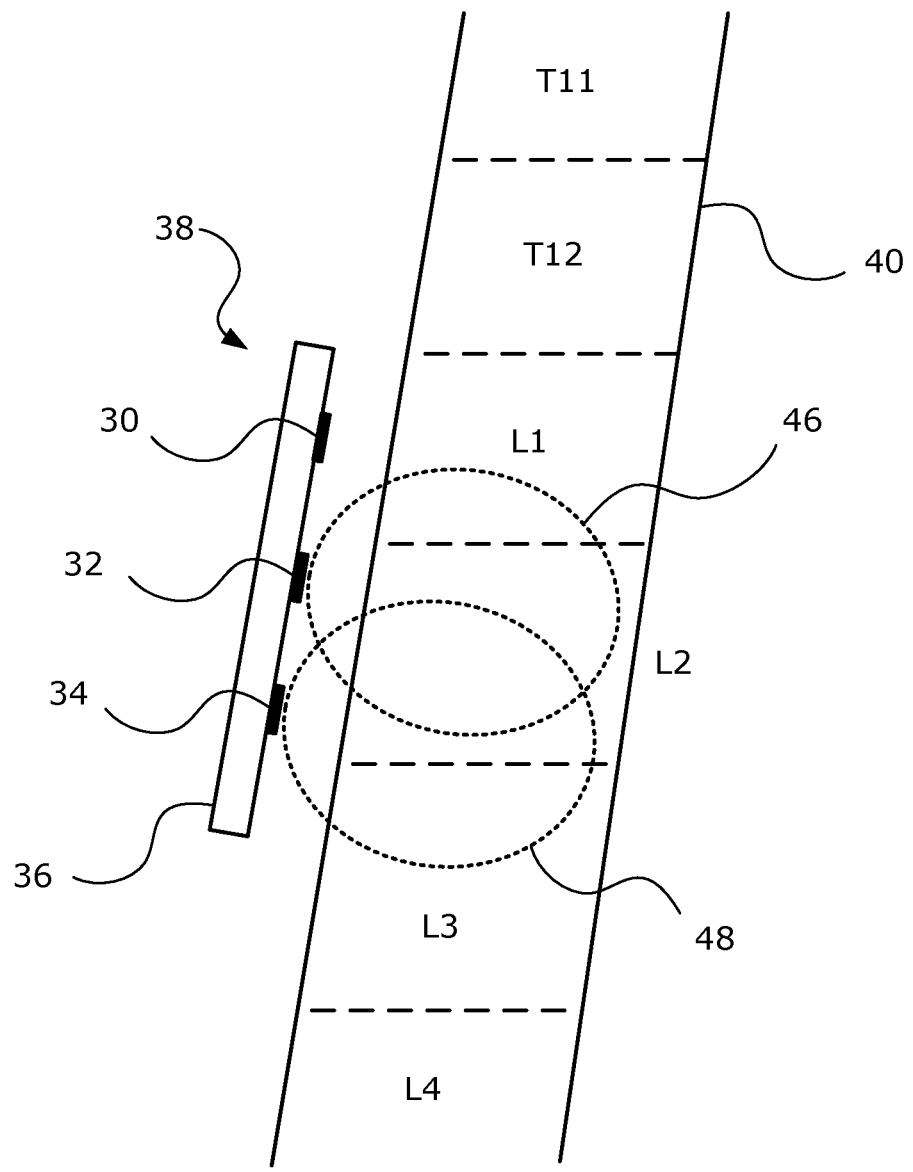
FIG. 6 shows an example of spinal cord neuromodulation being targeted to a specific spinal cord level.

For example, FIG. 4 shows a patient that is experiencing pain in area 20 of their body. The user (e.g., the patient or a caretaker) enters the location of area 20 into the tool and the tool correlates this area 20 with the L2 dermatome level on the left side, and then correlates the left-side L2 dermatome level with the corresponding region the spinal cord or the vertebral level that corresponds to the L2 level of the spinal cord. FIG. 6 shows an image of the spinal cord 40 with the spinal cord levels being represented as different functional regions in the spinal cord (levels T11-L4 being shown here). Adjacent the spinal cord 40 is an electrode 38 having three electrode contacts 30, 32, and 34 fixed on a lead body 36. Based on the user's input, the functional region L2 of spinal cord 40 is selected as the target region for electrical neuromodulation. Accordingly, the tool determines a set of electrode neuromodulation settings that would create a volume of activation that is directed to functional region L2. In this instance, the set of electrode neuromodulation settings includes the selection of electrode contacts 32 and 34 for activation, and electrode contact 30 for non-activation. Additionally, with this selected set of electrode neuromodulation settings, electrode 32 is predicted to create a volume of activation 46 and electrode 34 is predicted to create a volume of activation 48. Thus, with the combination of volume of activations 46 and 48, the selected set of electrode neuromodulation settings create a volume of activation that is directed to dermatome level L2 of the spinal cord. FIG. 5 shows a flowchart illustration of the above process.

Dermatome targeting using patient feedback about where the electrically-induced parasthesia is located in their body may not always be reliable because the patient's sensory perception may not be accurate or the patient may not sense sufficient parasthesia from the electrical neuromodulation. In certain embodiments, the dermatome location of the electrical neuromodulation can be localized more precisely using electromyography (EMG). For EMG localization of electrical neuromodulation, a number of EMG electrodes are placed on the patient's body. Electrical neuromodulation of the sensory fibers in the spinal cord can elicit a reflexive motor response and these motor responses can be detected as EMG signals in the specific dermatomes. Thus, by analyzing the EMG signals during electrical neuromodulation, the dermatome location of the electrical neuromodulation can be identified more precisely, thus allowing more accurate targeting of electrical neuromodulation.

In certain embodiments, the electrode used in the neuromodulation may also have recording electrodes which can sense neural signals passing through sensory nerve fibers. This can be useful for improved accuracy in identifying where the patient is experiencing pain or discomfort. The sensory signals passing through these sensory fibers may be produced by applying a sensory stimulation to the area where the patient is feeling the pain or discomfort. A variety of different kinds of sensory stimulations can be used, such as applying a dull touch, a sharp prick, or a slight electrical pulse to the skin. The recording electrode could sense this signal being transmitted along nearby sensory fibers as an increase in local field potential. Based on which recording contact records the strongest signal, or based on the distribution of the signal across multiple contacts, the fiber(s) carrying the sensory stimulation signal from the afflicted dermatome is identified. Moreover, the strength of the signal can be used to determine the magnitude of the patient's pain or discomfort in that area.

Cerebrospinal Fluid

One of the factors influencing the electric field generated by an electrode is the electrical conductivity of the surrounding tissue medium (e.g., the electrical conductivity of the spinal cord neural tissue or other body tissue in the vicinity of the electrode, such as cerebrospinal fluid, tissue membranes, encapsulation tissue around the electrode, etc.). Thus, the electric field model used by the tool may include a characterization of the tissue electrical conductivity. In some cases, different anatomical structures may be represented as having different electrical conductivities in the electric field model. One of the tissue mediums that may be relevant in spinal cord neuromodulation is the cerebrospinal fluid (CSF) that surrounds the spinal cord. The CSF is considered to be relatively more electrically conductive compared to the other surrounding tissue.

In certain embodiments, the electric field model may account for the amount of CSF that is present between the electrode and the spinal cord. For example, the electric field model may account for the thickness (in dimensional terms, not viscosity) of the CSF between the electrode and the spinal cord. The dimensional thickness of the CSF can be determined using various approaches. In some cases, the thickness of the CSF can be determined by using a radiologic image, such as an axial view MR image. In some cases, the thickness of the CSF can be approximated based on the electrode position relative to the spinal anatomy. For example, the thickness of the CSF can be approximated based on the vertebral level where the electrode is positioned or the size of the vertebrae where the electrode is positioned (in general, the size of the vertebral bodies progressively increase moving from the cervical to the lumbar spine). Accounting for the electrical conductivity of CSF may allow the tool to calculate a more accurate the volume of activation.

Total Potential Volume of Activation

In certain embodiments, the tool can show the total potential volume of activation capable of being produced by an electrode at a given position. The total potential volume of activation can be displayed as the overlap of the volume of activations produced by the highest tolerable amplitude anode/cathode pulse for each electrode. Knowing the total potential volume of activation may be useful during initial surgical implantation of the electrode to help position the electrode at a location that will meet both current and possible future coverage needs (e.g., accounting for the possibility of electrode migration, worsening pain, or wider extent of pain). The feature can also be useful for quickly seeing how much area has been tested by overlaying a history of stimulated regions and the total potential volume of activation. This feature can also allow the user to view spaces that are outside the potential volume of activation for a given electrode placement. For example, if two electrodes are staggered or canted, they may leave regions of the spinal cord unable to be reached by electrical neuromodulation. Displaying the total potential volume of activation would allow this to be realized during intraoperative or postoperative programming.

This display of the total potential volume of activation can be turned on and off, and may appear in a variety of colors, gradients, and patterns to best suit visualization. In addition, it may be layered with current neuromodulation settings or previously trialed settings to compare the total potential volume of activation with volumes already tested. As with other display features, the total potential volume of activation can be displayed as a two-dimensional area on a spinal cord or as a three-dimensional volume. The total potential volume of activation may also be used to predict dermatome regions capable of neuromodulation, which would then be displayed on a two-dimensional or three-dimensional representation of the spinal cord. The total potential volume of activation could also be shown as all the dermatome regions capable of being affected by the neuromodulation, which could be displayed on an image of a human figure.

Functional Midline

When multiple electrodes (two or more) are implanted into a patient, the electrodes are often not parallel to each other or not in level alignment with each other (e.g., one is higher than the other), and moreover, the position of the electrodes relative to the spinal cord is often not known since the spinal cord may not be visible on x-ray images. Where multiple electrodes are being modeled by the tool, the tool may determine a functional midline in the neuromodulation space around the electrodes. The functional midline is an imaginary line running in the neuromodulation space of the electrodes, which corresponds to the sensory midline of the patient's body, and which could be aligned to the physiologic midline of the patient's spinal cord. The functional midline is established by finding a set of neuromodulation settings that induces parasthesia in the center of the patient's body. The functional midline can then be derived from the relative pulse intensities between the multiple electrodes. The tool may also determine the functional midline for a paddle-type electrode having an array of electrode contacts on a single electrode lead or a single electrode that is implanted in a lateral orientation.

Figure 7A:
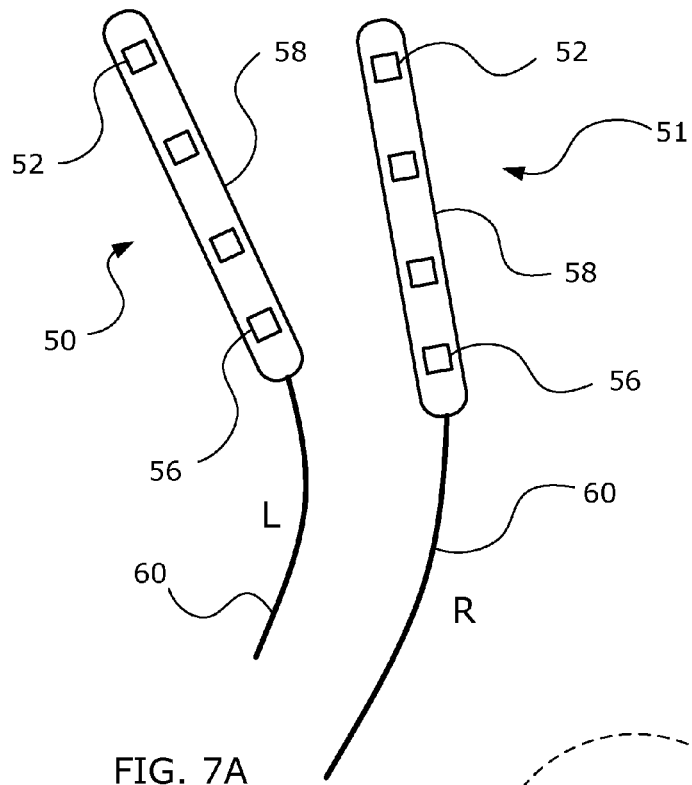
FIGS. 7A and 7B demonstrate an example of how the functional midline of two electrodes can be determined.
Figure 7B:
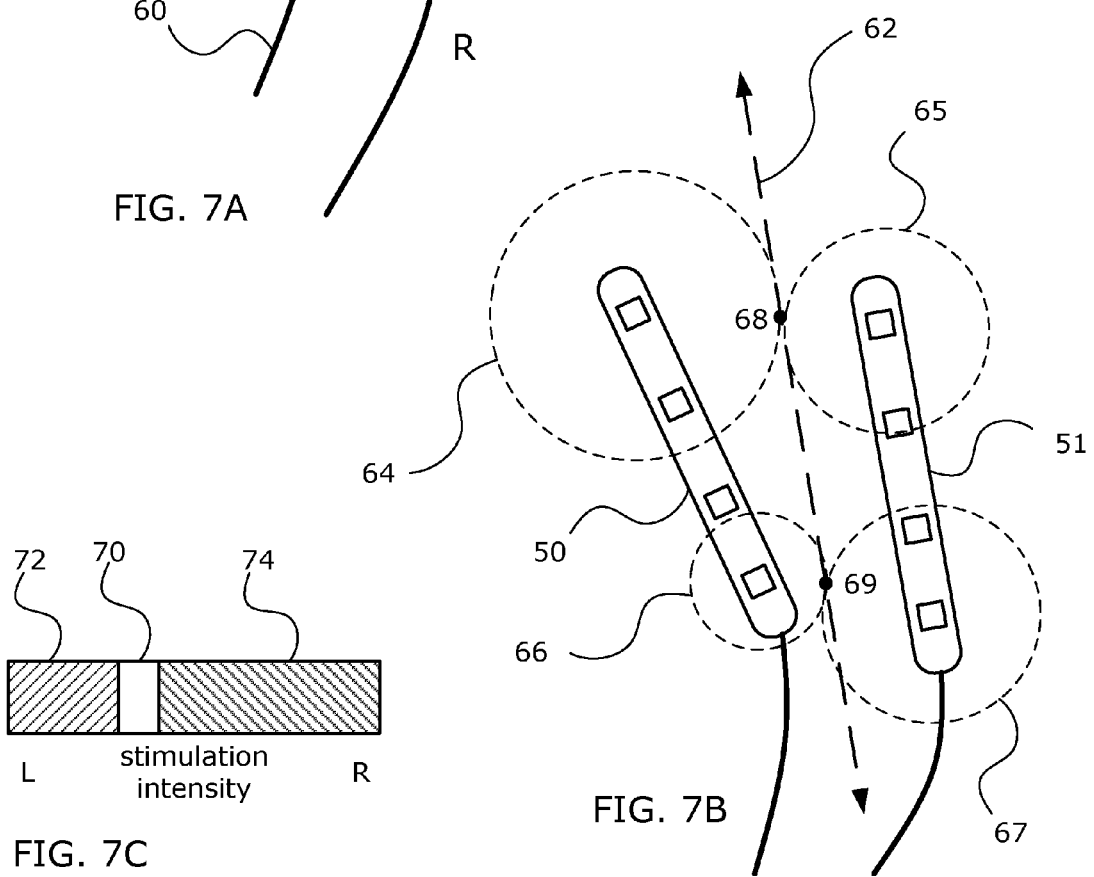
Figure 7C:
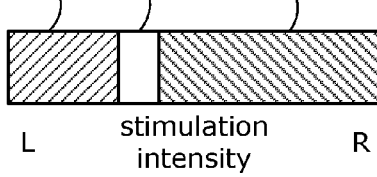
FIG. 7C shows a slider bar that may be used by the tool for adjusting spinal cord neuromodulation.

An example of how this may be performed is illustrated in FIGS. 7A and 7B. FIG. 7A shows two electrodes, 50 on the left side and 51 on the right side, each comprising a lead body 58 connected to lead wires 60 and having three electrode contacts, including top-most contacts 52 and bottom-most contacts 56. The functional midline is determined by finding the functional midpoint between the left and right top-most electrode contacts 52, and the left and right bottom-most electrode contacts 56. The functional midpoint between the left and right top-most electrode contacts 52 is determined by varying the relative pulse intensities (monopolar) between the left and right top-most electrode contacts 52, and receiving patient feedback of where the parasthesia is being sensed. FIG. 7C shows how the stimulation field can be shifted to the left or right using a slider 70 displayed by the tool. Slider 70 is inside a bar that represents the left versus right relative pulse intensity. Area 72 in the bar corresponds to the relative pulse intensity for the electrode contact on the left electrode and area 74 in the bar corresponds to relative pulse intensity for the counterpart electrode contact on the right electrode. Slider 70 can be moved left or right to adjust the pulse intensity that is apportioned between the left and right electrode contacts. As an initial setting, the slider may be positioned in the middle such that half of a tolerable pulse intensity is sent to each of the counterpart electrode contacts on the left and right electrodes.

Figure 10:
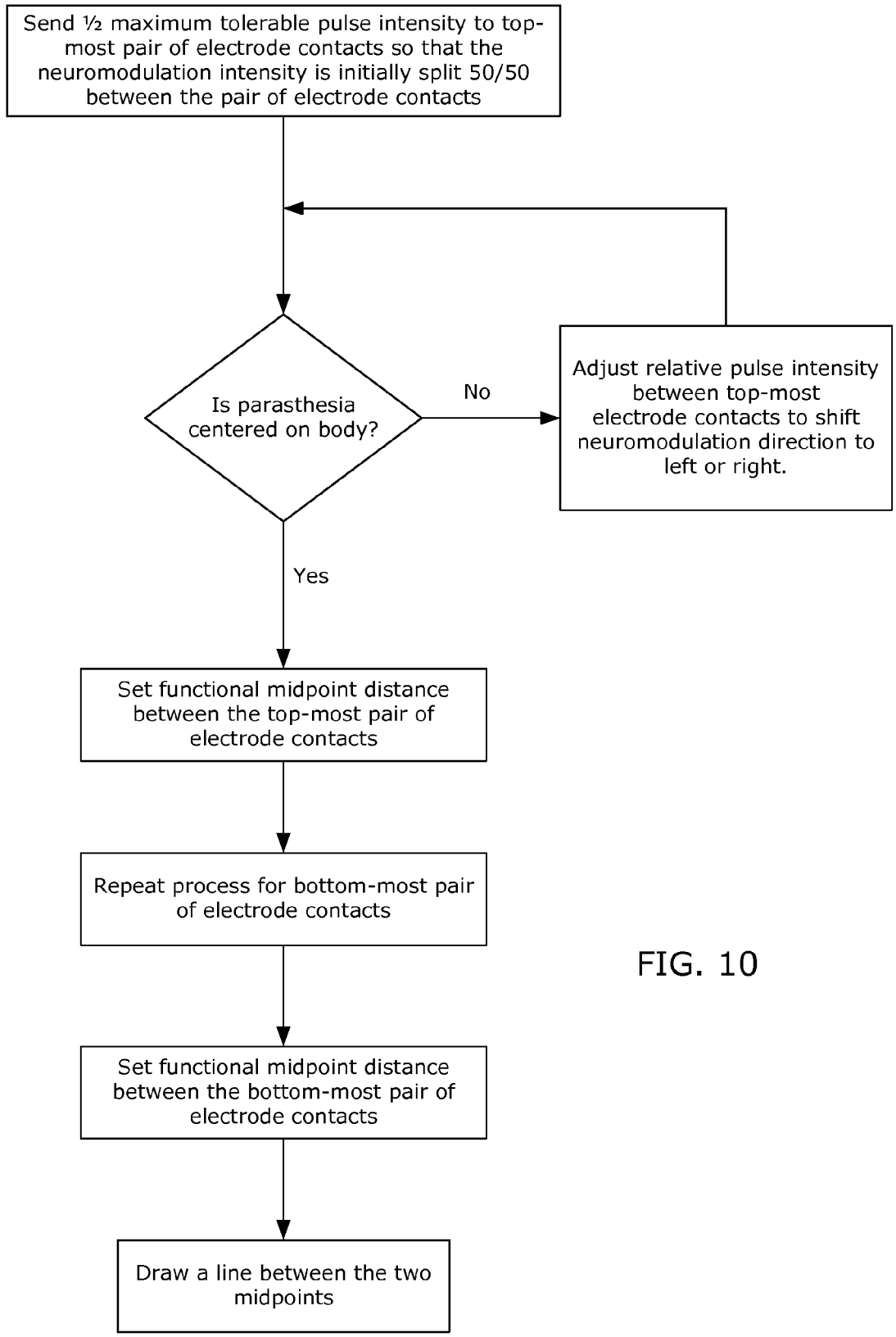
FIG. 10 shows a flowchart illustrating an example of how the functional midline of two electrodes can be determined.

When the patient indicates that the parasthesia is being sensed in the center of their body, the relative pulse intensities of the left and right top-most electrode contacts 52 gives the proportionate distance of the functional midpoint from the respective left and right electrode contacts 52. As shown in FIG. 7B, the patient's parasthesia has been centered for the top-most electrodes 52 when the left top-most electrode contact has a pulse intensity 64 and the right top-most electrode has a pulse intensity 65, with the functional midpoint being at point 68. Pulse intensities 64 and 65 do not represent actual activation fields, but is being used only to help illustrate how the left versus right relative pulse intensities can differ and be used to find the midpoint. The same process of varying the left/right relative pulse intensities and receiving patient feedback about the location of the parasthesia is repeated to find the functional midpoint for the bottom-most electrode contacts 56. In this instance, the patient's parasthesia has been centered for the bottom-most electrodes 56 when the left bottom-most electrode contact has a relative pulse intensity 66 and the right bottom-most electrode contact has a relative pulse intensity 67, with the functional midpoint being at point 69. An imaginary line is drawn between functional midpoints 68 and 69, and this imaginary line is the functional midline 62 between electrodes 50 and 51. FIG. 10 shows a flowchart illustration of the above process.

Figures 8A, 8B:
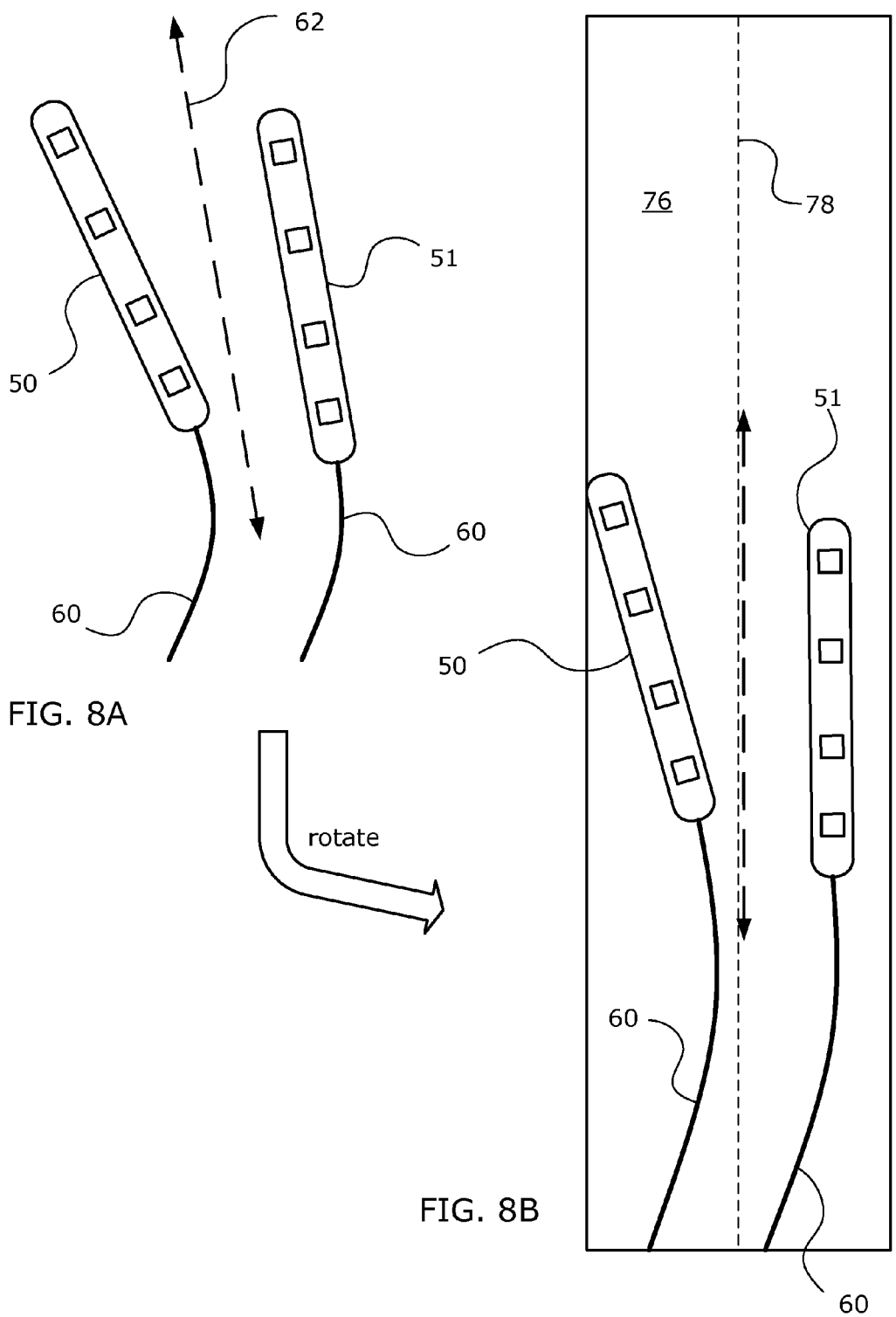
FIGS. 8A and 8B show an example of how the functional midline of the electrodes can be aligned with the physiologic midline of the spinal cord.
Figure 9:
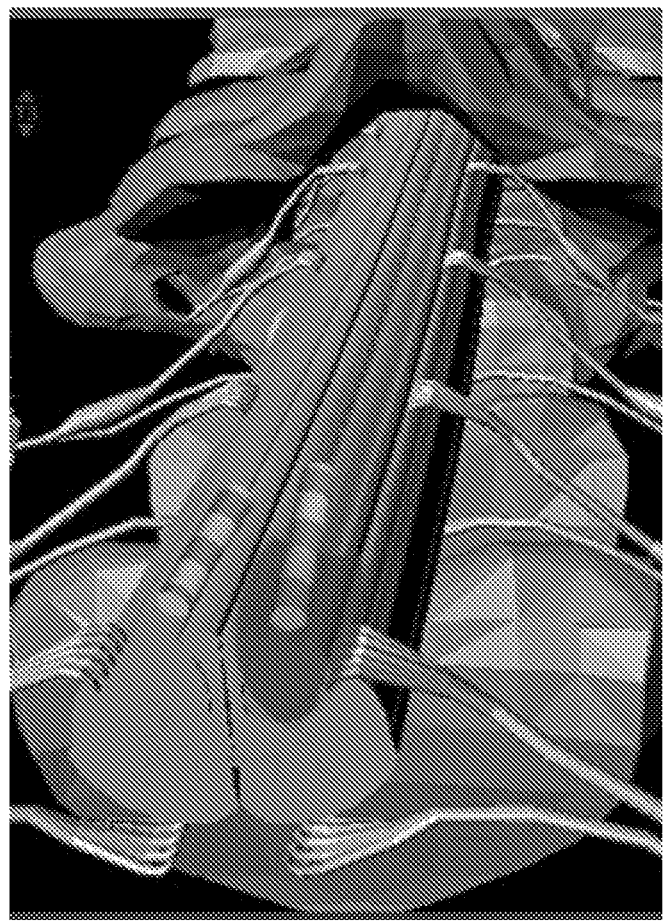
FIG. 9 shows an example of how electrodes can be displayed with an image of the spinal cord.

Once the functional midline is determined, this information can be used in various ways to assist in electrical neuromodulation of a patient's spinal cord. One use for the functional midline is for aligning the electrodes with respect to the physiologic midline of the spinal cord. For example, FIG. 8A shows the two electrodes 50 and 51 again with their functional midline 62. Based on this functional midline 62, the position (including orientation) of electrodes 50 and 51 can be aligned with a spinal cord. FIG. 8B shows a graphically rendered, generic image of a spinal cord 76 (not specific to any particular patient), with its physiologic midline represented by dotted line 78. By rotating the pair of electrodes 50 and 51, their functional midline 62 is made to be oriented parallel to physiologic midline 78 of spinal cord 76. The two electrodes 50 and 51 are displayed over spinal cord 76 to give a more accurate representation of how the electrodes 50 and 51 are oriented relative to the actual patient's spinal cord. FIG. 9 shows another example of how electrodes and a graphically rendered, generic image of a spinal cord could be displayed by the tool.

Thus, in certain embodiments, the tool receives a radiologic image of the patient showing one or more electrodes inside the patient and locates the one or more electrodes in the radiologic image. The one or more electrodes collectively have multiple electrode contacts. The tool determines the functional midline for the one or more electrodes and may display on a display screen, an image of a spinal cord and the one or more electrodes such that the functional midline of the one or more electrodes is aligned to the physiologic midline of the spinal cord.

In some cases, the tool may receive information about the relative electrical neuromodulation intensity between a first electrode contact among the multiple electrode contacts and a first counterpart electrode contact among the multiple electrode contacts. Based on the relative electrical neuromodulation intensities, the tool can determine a first midpoint between the first electrode contact and the first counterpart electrode contact. The tool may further receive information about the relative electrical neuromodulation intensity between a second electrode contact among the multiple electrode contacts and a second counterpart electrode contact among the multiple electrode contacts. Based on the relative electrical neuromodulation intensities, the tool can determine a second midpoint between the second electrode contact and the second counterpart electrode contact. The functional midline can be established as the line between the first midpoint and the second midpoint. This method may be applied to a single electrode (e.g., a paddle-type electrode having multiple electrode contacts arranged in an array) or multiple separate electrodes.

In cases where there are multiple separate electrodes (which collectively have multiple electrode contacts), a functional midline may be found using a first electrode contact which is on a first one of the multiple electrodes and a first counterpart electrode contact on a second one of the multiple electrodes. Based on the relative electrical neuromodulation intensities, the tool can determine a first midpoint between the first electrode contact and the first counterpart electrode contact. Furthermore, the tool may receive information about the relative electrical neuromodulation intensity between a second electrode contact on the first one of the multiple electrodes and a second counterpart electrode contact on the second one of the multiple electrodes. Based on the relative electrical neuromodulation intensities, the tool can determine a second midpoint between the second electrode contact and the second counterpart electrode contact; and establish the functional midline as a line between the first midpoint and the second midpoint.

Adaptive Searching

The functional midline can also be used to assist in targeting of the spinal cord neuromodulation to the appropriate side of the body (right vs. left side). Based on whether the patient's symptoms are on the left or right side of their body, the electrical neuromodulation to the spinal cord can be directed to the same side (left or right) of the functional midline. This targeting may be implemented through a binary searching algorithm.

Figure 11A:
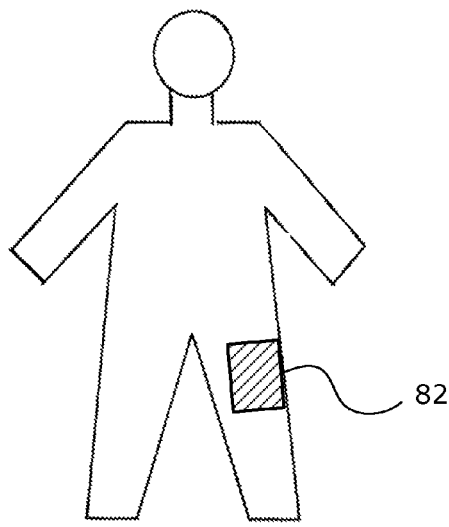
FIGS. 11A-11D show an example of how the tool can use the functional midline for targeting of spinal cord neuromodulation.
Figure 11B:
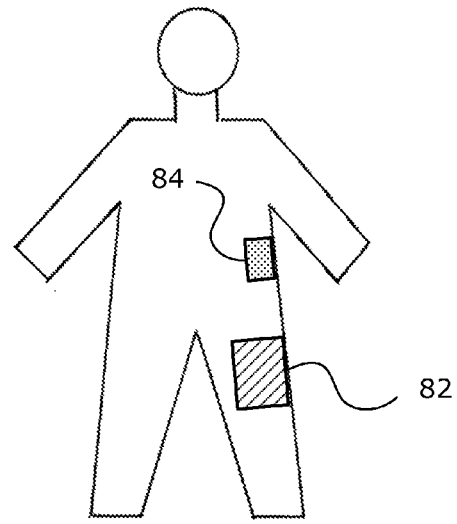
Figure 11C:
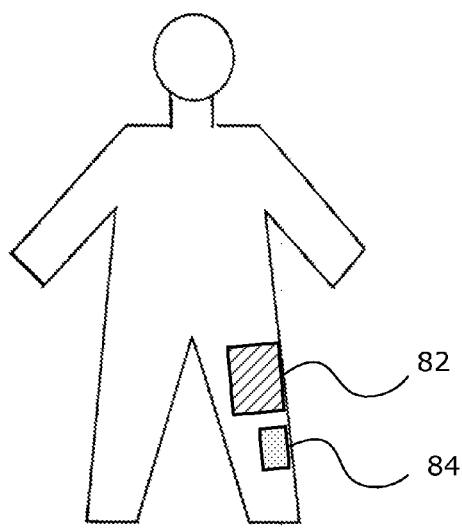
Figure 11D:
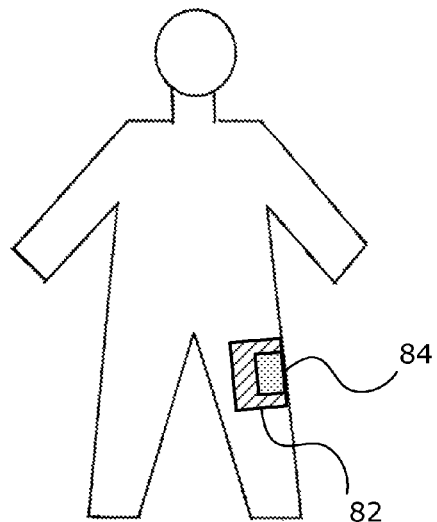

For example, FIGS. 11A-11D show one example of how this binary searching algorithm can be applied. In this particular example, two electrodes have been implanted in the patient's spine, and the tool has determined the functional midline between the two electrodes in the manner described above. The tool receives the location of where the patient is experiencing pain; in this particular case, the left thigh. As shown in FIG. 11A, an area 82 of the left thigh is shown on the display screen as the area where the patient is experiencing pain. With the pain being located on the left side, one or more of the electrode neuromodulation settings are configured to apply neuromodulation to the left side of the spinal cord based on the functional midline of the two electrodes. The patient then indicates where the neuromodulation-induced parasthesia is being felt. In this instance, the patient indicates that the parasthesia is felt on the left abdomen, which is shown as parasthesia area 84 in FIG. 11B. Because the parasthesia area 84 is too high above the targeted pain area 82, the electrode neuromodulation settings are adjusted to direct neuromodulation to an area lower on the spinal cord. After this adjustment, the patient again indicates where the neuromodulation-induced parasthesia is being felt. In this instance, as shown in FIG. 11C, the patient indicates that the parasthesia area 84 is being felt on the left calf below the pain area 82. As shown in FIG. 11D, with further adjustments to the neuromodulation settings, the area of parasthesia 84 is now within the area of pain 82. Since this area of parasthesia 84 is not sufficient to cover the entire area of pain 82, the pulse intensity may need to be increased to achieve sufficient reduction in pain.

Electrode Migration

One of the problems associated with spinal cord neuromodulation is changes in the position of the electrode after its implantation. For example, the electrode may migrate to a different location (e.g., move downwards or move to the side in a "windshield-wiper" fashion) or change its orientation (e.g., the long axis of the electrode may tilt to a different direction, or in the case of a directional electrode contact, rotate towards a different direction). This change in the position of the electrode can result in a loss of therapeutic efficacy. In certain embodiments, the tool of the present invention can adjust the neuromodulation settings to accommodate for the change in electrode position. A change in the position of the electrode can be detected on a radiologic image, such as x-ray images, in the manner described above.

In some cases, the tool may compare the position of the electrode in a radiologic image taken prior to migration of the electrode (e.g., a post-operative x-ray) to the position of the electrode after migration. Based on the relative positioning of the electrode before and after migration, the tool can adjust one or more of the electrode neuromodulation settings to redirect the neuromodulation to the original target. In the example shown in FIG. 12A, an electrode comprising a lead body 96 and three electrodes 93, 94, and 95 are shown prior to migration. At this position, electrode contact 95 is activated to produce a volume of activation 97 that is directed to target site 92 on spinal cord 90.

Figure 12A:
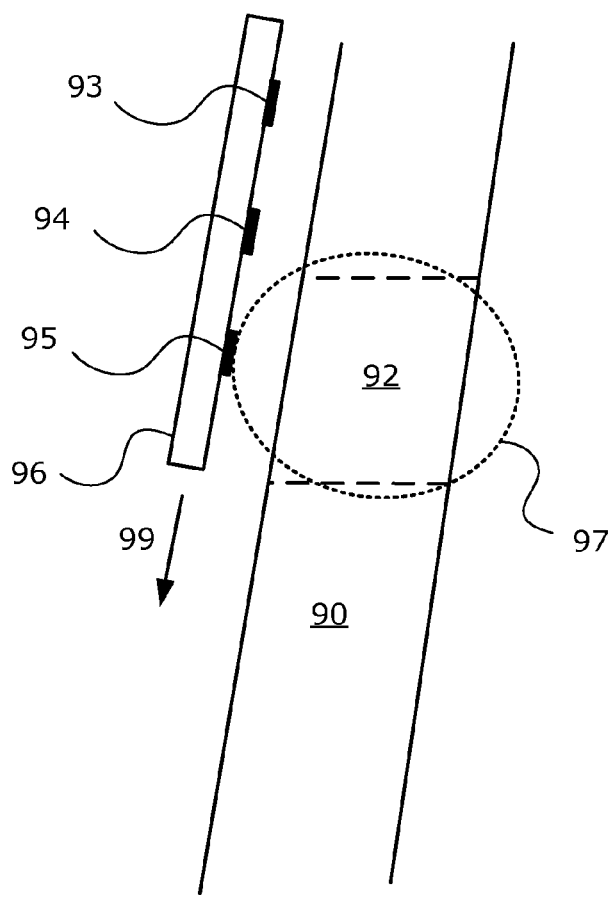
FIGS. 12A and 12B demonstrate an example of how the neuromodulation settings can be adjusted to accommodate for a change in electrode position.
Figure 12B:
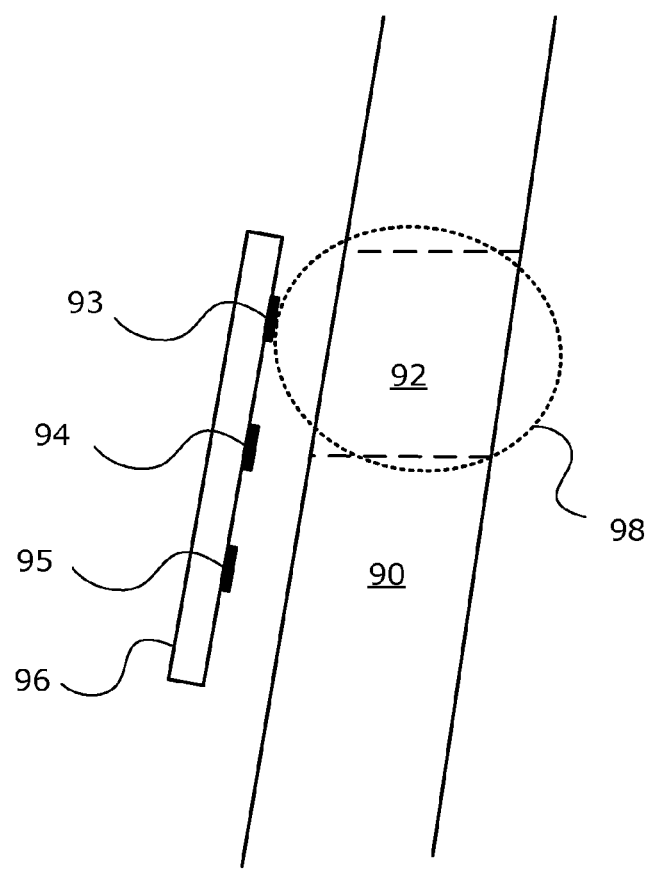
Figure 13:
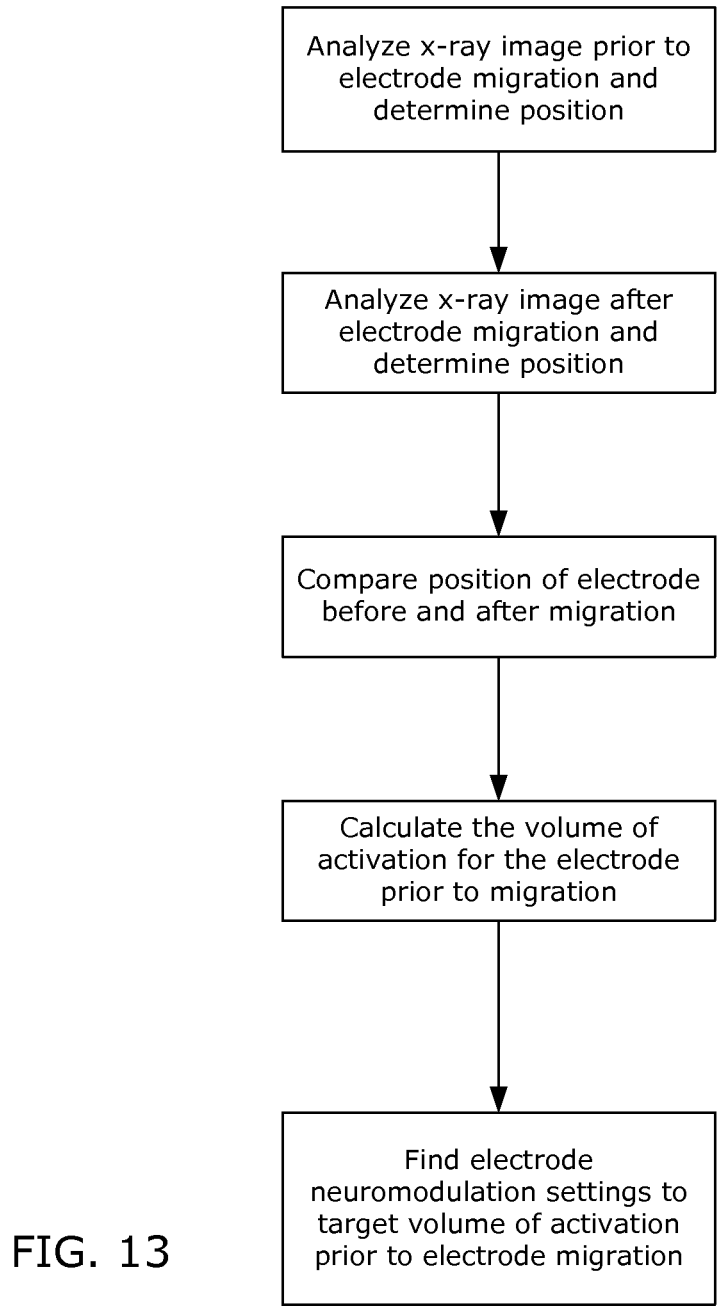
FIG. 13 shows a flowchart illustrating an example of how the neuromodulation settings can be adjusted to accommodate for a change in electrode position.

FIG. 12B shows the same electrode after downward migration along spinal cord 90 (see arrow 99 in FIG. 12A). Because of this migration, the prior neuromodulation settings are ineffective because the electrode has shifted relative to target site 92. But by comparing the relative position of the electrode before and after migration, the electrical neuromodulation settings may be adjusted to redirect the electrical neuromodulation to the original target site 92. Using the targeting methods described above, the tool finds a set of neuromodulation settings with the selection of electrode contact 93 that creates a volume of activation 98 that overlaps with target site 92 or volume of activation 97. As a result, the tool has accommodated the electrical neuromodulation for electrode migration. FIG. 13 shows a flowchart illustration of the above process. Positional changes in the electrodes can also be determined from means other than by radiologic imaging. For example, the electrode may have an accelerometer that detects the position of the electrode. The tool may determine positional changes in the electrode based on the information from the accelerometer.

Thus, in certain embodiments, the tool receives a first radiologic image of an electrode inside a patient, wherein the electrode is in a first position. The tool further receives a second radiologic image of the electrode after a change in the electrode's position, wherein the electrode is in a second position. The tool determines the position of the electrode in the second position relative to the electrode in the first position and calculates a first volume of activation generated by the electrode in the first position. The tool can then determine an electrode neuromodulation setting for the electrode in the second position that produces a second volume of activation that at least partially encompasses the first volume of activation. The tool may display the second volume of activation on a display screen.

In some cases, the tool calculates multiple test volumes of activation using different electrode neuromodulation settings and compares the multiple test volumes of activation to the first volume of activation. Based on the comparison of the multiple test volumes of activation, the tool selects an electrode neuromodulation setting for the electrode in the second position that produces the second volume of activation.

Automated Serial Review of Electrode Contacts

In certain embodiments, the tool may also have a programming mode that automates the standard monopolar review process. In this mode, the user is asked to identify the pain location and severity. Then, each consecutive electrode contact is activated at a tolerable amplitude. The patient is asked to identify the location of the parasthesia and what level of pain they are currently feeling. This is repeated for each available electrode contact. Once each contact has been tested, the user may be given the option of having the tool interpolate the mapped data to predict the best neuromodulation settings. SFMs may be computed and displayed for each successive activation and displayed in real-time to the user, together with real-time display of the parasthesia locations on a three-dimensional model. Real-time display of SFMs and parasthesia locations may also be performed in other programming modes (e.g., the manual programming mode described below in connection with the interface features).

Software and Machine Embodiments

The tool of the present invention may also be embodied as a computer-readable storage medium having executable instructions for performing the various processes as described herein. The storage medium may be any type of computer-readable medium (i.e., one capable of being read by a computer), including non-transitory storage mediums such as magnetic or optical tape or disks (e.g., hard disk or CD-ROM), solid state volatile or non-volatile memory, including random access memory (RAM), read-only memory (ROM), electronically programmable memory (EPROM or EEPROM), or flash memory. The term "non-transitory computer-readable storage medium" encompasses all computer-readable storage media, with the sole exception being a transitory, propagating signal.

The tool of the present invention may also be embodied as a computer system that is programmed to perform the various processes described herein. The computer system may include various components for performing these processes, including processors, memory, input devices, and/or displays. The computer system may be any suitable computing device, including general purpose computers, embedded computer systems, network devices, or mobile devices, such as handheld computers, laptop computers, notebook computers, tablet computers, and the like. The computer system may be a standalone computer or may operate in a networked environment.

Interface Features

The tool may use any of a variety of interface features for interacting with a user. These interactions may include receiving inputs, producing outputs, displaying information, storing program settings, making selections (e.g., target sites, neuromodulation settings, etc.), and the like. The interface features may be adapted for any of the various potential users of the tool, including clinicians, care providers, technicians, salespeople, or the patients themselves. The interface may be provided through any suitable hardware devices, including touch screens, touch pads, mouse, trackball, buttons, wheels, dials, etc. For example, the tool may display a three-dimensional human figure the user may be able point to and select a part of the human figure by a touch screen or a mouse. Various types of interface features which may be used by the tool include those described in U.S. Patent Application Publication No. 2009/0287271 (Blum et al.), which is incorporated by reference herein. The tool may display on a display screen any of the elements described above, including the volumes of activation, spinal anatomy (e.g., of the vertebrae, spinal cord, or both), radiologic images, electrodes, human figures, and such, either individually or in combination.

The tool may also have a manual programming mode in which previously trialed neuromodulation settings are displayed. Another feature may allow the user to customize a neuromodulation region, and then drag the region to the area of the spinal cord for trial simulations of neuromodulation; or allow the user to attempt neuromodulation settings believed to be advantageous by offering a specific visual history of previously attempted settings. The recorded results of the previously attempted settings may be displayed in two or three-dimensional space. For example, the patient's pain zone can be displayed on a three-dimensional model together with the parasthesia zones that resulted from a set of attempted settings. The three-dimensional model may be displayed in conjunction with the display of SFMs calculated for the set of attempted settings (e.g., in a separate display area that shows a three-dimensional model of the spinal cord). The patient's pain zone can be mapped on the human figure and distinguished in some way (by color, for example). The previous parasthesia zones from trial simulations can appear on the human figure. These zones may directly show a result, such as efficacy or indication of pain, by a different color or shade, or they may have text that appears inside them or in a pop-up when the user hovers or clicks the computer's pointing mechanism over the region. Example text may include Visual Analogue Scale (VAS) scores and stimulation settings. The corresponding volume of activation shown on the spinal cord could also be highlighted or identified when the user selects the affected dermatome. This feature would allow the user to easily see which dermatomes are impacted by the neuromodulation zones, and vice versa.

After viewing the results the user may wish to trial a volume of activation that has not been previously trialed. The manual programming mode in the tool can feature a simple method to trial an area of the spinal cord by entering a mode that displays a desired volume of activation that can be manipulated by the user. Alternatively, the user could start with a previously trialed volume of activation. The desired volume of activation may be resized and dragged to the desired location on the spinal cord image. An algorithm would then calculate the closest actual neuromodulation settings that would best fit the zone desired for neuromodulation (i.e., adjusting the settings associated with the previously trialed volume of activation to levels that are appropriate for the resized/re-located volume) and show the user the new settings, who would confirm and trial the neuromodulation. The calculation of the new settings may be performed in a similar fashion to the method previously described for adjusting settings in response to unintended electrode migration, i.e., creating a volume of activation that overlaps with the new volume. The algorithm may take into consideration factors pertaining to the new location, such as CSF thickness, when calculating the new settings. Since it may be advantageous to view the depth of tissue affected by the neuromodulation, a slidable bar can be featured along the side of the posterior spinal cord view. The bar may be positioned to the precise location that a cross-sectional view is desired. In the cross-sectional view, the slidable bar could be used to sequentially browse through different cross-sectional views. Once positioned, the bar is selected or clicked to bring a cross-sectional view that displays the desired volumes of activation as well as offers the same feature of using a desired volume of activation that can be manipulated by the user.

Once results of the manual programming mode are optimized, the final settings may be saved to memory, named, and the user is returned to the main programming page. Saved settings may be selected and displayed via an interface menu. Settings may be merged to combine a plurality of saved settings into a single set of saved settings. For example, settings targeting different pain zones may be combined in order to provide a custom course of treatment for a patient experiencing pain in more than one zone. Similarly, settings that by themselves fail to provide adequate pain zone coverage may be combined to provide sufficient coverage.

The foregoing description and examples have been set forth merely to illustrate the invention and are not intended as being limiting. Each of the disclosed aspects and embodiments of the present invention may be considered individually or in combination with other aspects, embodiments, and variations of the invention. Further, while certain features of embodiments of the present invention may be shown in only certain figures, such features can be incorporated into other embodiments shown in other figures while remaining within the scope of the present invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

What is claimed is:

1. A method for assisting planning or performing of neuromodulation in a patient, comprising:
   receiving a first radiologic image showing an electrode and an anatomic region of the patient;
   receiving a second radiologic image showing the electrode and the anatomic region of the patient, wherein the second radiologic image provides a different view than the first radiologic image;
   using the first radiologic image and the second radiologic image to determine a three-dimensional position of the electrode in relation to the anatomic region; and
   displaying the electrode and a display image of the anatomic region on a display screen.

2. The method of claim 1, wherein the first radiologic image and second radiologic image show multiple electrodes, and further comprising:
   using the first radiologic image and the second radiologic image to determine the three-dimensional position of the multiple electrodes in relation to each other.

3. The method of claim 1, wherein the first radiologic image and second radiologic image are x-ray images.

4. The method of claim 3, wherein the first radiologic image is an anterior-posterior view x-ray image and the second radiologic image is a lateral view x-ray Image.

5. The method of claim 1, wherein the anatomic region is a spinal anatomy of the patient.

6. The method of claim 1, further comprising:
   determining a functional midline for the electrode; and
   displaying on the display screen, an image of the anatomic region and the electrode such that the functional midline of the electrode is aligned to a physiologic midline of the anatomic region.

7. The method of claim 6, wherein the anatomic region is a spinal cord.

8. A computer system that is programmed to perform steps that comprise:
   receiving a first radiologic image showing an electrode and an anatomic region of the patient;
   receiving a second radiologic image showing the electrode and the anatomic region of the patient, wherein the second radiologic image provides a different view than the first radiologic image; and
   using the first radiologic image and the second radiologic image to determine a three-dimensional position of the electrode in relation to the anatomic region.

9. The method of claim 8, wherein the anatomic region is a spinal anatomy of the patient.

10. The method of claim 6, wherein determining the functional midline comprises:
    receiving information about a first relative electrical neuromodulation intensity between a first electrode contact among multiple electrode contacts and a first counterpart electrode contact among the multiple electrode contacts; and
    based on the first relative electrical neuromodulation intensity, determining a first midpoint between the first electrode contact and the first counterpart electrode contact.

11. The method of claim 10, wherein determining the functional midline further comprises:
    receiving information about a second relative electrical neuromodulation intensity between a second electrode contact among the multiple electrode contacts and a second counterpart electrode contact among the multiple electrode contacts;
    based on the second relative electrical neuromodulation intensity, determining a second midpoint between the second electrode contact and the second counterpart electrode contact; and
    establishing the functional midline as a line between the first midpoint and the second midpoint.

12. The method of claim 10, wherein multiple electrodes are located in the first radiologic image; and wherein the first electrode contact is on a first one of the multiple electrodes and the first counterpart electrode contact is on a second one of the multiple electrodes.

13. The method of claim 12, wherein determining the functional midline further comprises:
    receiving information about a second relative electrical neuromodulation intensity between a second electrode contact on the first one of the multiple electrodes and a second counterpart electrode contact on the second one of the multiple electrodes;
    based on the second relative electrical neuromodulation intensity, determining a second midpoint between the second electrode contact and the second counterpart electrode contact; and
    establishing the functional midline as a line between the first midpoint and the second midpoint.

14. The method of claim 12, further comprising determining a relative position of the multiple electrodes in relation to each other.

15. The method of claim 10, wherein the first relative electrical neuromodulation intensity between the first electrode contact and the first counterpart electrode contact is an electrode neuromodulation setting that produces a parasthesia that is centered on the patient's body.

16. The computer system of claim 8, wherein the computer system is further programmed to perform actions that comprise:
    determining a functional midline for the electrode.

17. A non-transitory computer-readable storage medium comprising instructions executable by a computer processor, the instructions which, when executed by the processor, cause the processor to perform a method, the method comprising:
    receiving a first radiologic image showing an electrode and an anatomic region of the patient;
    receiving a second radiologic image showing the electrode and the anatomic region of the patient, wherein the second radiologic image provides a different view than the first radiologic image; and
    using the first radiologic image and the second radiologic image to determine a three-dimensional position of the electrode in relation to the anatomic region.

18. The method of claim 17, wherein the anatomic region is a spinal anatomy of the patient.

19. The non-transitory computer-readable storage medium of claim 17, wherein the instructions, when executed by the processor, further cause the processor to perform actions, the actions comprising:
    determining a functional midline for the electrode.

* * * * *